(12) United States Patent
Gabay et al.

(10) Patent No.: US 12,390,179 B2
(45) Date of Patent: Aug. 19, 2025

(54) TEMPORAL DATA GENERATION WITH SCATTERED X-RAY RADIATION

(71) Applicant: LightLab Imaging, Inc., Westford, MA (US)

(72) Inventors: Eyal Gabay, Kfar-Saba (IL); Vitaly Gavensky, Atlit (IL); Jacob Segev, Haifa (IL); Yaroslav Shevchinsky, Kiryat Yam (IL); Dov Chanoch Waisman, Haifa (IL); Yuval Vaknin, Hanaton (IL)

(73) Assignee: LightLab Imaging, Inc., Westford, MA (US)

( * ) Notice: Subject to any disclaimer, the term of this patent is extended or adjusted under 35 U.S.C. 154(b) by 197 days.

(21) Appl. No.: 17/972,969

(22) Filed: Oct. 25, 2022

(65) Prior Publication Data

US 2023/0125217 A1    Apr. 27, 2023

Related U.S. Application Data

(60) Provisional application No. 63/271,524, filed on Oct. 25, 2021.

(51) Int. Cl.
| | |
|---|---|
| *A61B 6/40* | (2024.01) |
| *A61B 6/00* | (2006.01) |
| *A61B 6/42* | (2024.01) |
| *A61B 6/46* | (2024.01) |
| *A61B 6/50* | (2024.01) |

(52) U.S. Cl.
CPC ............ *A61B 6/483* (2013.01); *A61B 6/4208* (2013.01); *A61B 6/461* (2013.01); *A61B 6/481* (2013.01); *A61B 6/504* (2013.01)

(58) Field of Classification Search
CPC ........ A61B 6/483; A61B 6/4208; A61B 6/461
See application file for complete search history.

(56) References Cited

U.S. PATENT DOCUMENTS

| | | | |
|---|---|---|---|
| 10,980,494 B2 * | 4/2021 | Lu | A61B 6/502 |
| 2004/0102693 A1 | 5/2004 | Jenkins | |
| 2008/0253523 A1 * | 10/2008 | Boyden | A61B 6/505 |
| | | | 378/87 |
| 2009/0152471 A1 * | 6/2009 | Rousso | G01T 1/161 |
| | | | 250/363.04 |

(Continued)

OTHER PUBLICATIONS

International Search Report and Written Opinion issued in Appln. No. PCT/US2022/047695 mailed Jan. 30, 2023 (12 pages).

*Primary Examiner* — Hugh Maupin
(74) *Attorney, Agent, or Firm* — Lerner David LLP

(57) ABSTRACT

Aspects of the disclosure provide for an x-ray detection device for detecting radiation scattered off of a target during an imaging procedure and generating temporal data indicating the time of occurrence of a pulse of radiation emitted towards the target. The temporal data can be sent to a host device and used to timestamp images generated from the pulses of radiation. The x-ray detection device is portable and can be installed in a catheterization laboratory or imaging environment to detect the occurrence of radiation, without occluding or partially occluding the beam source. Aspects of the disclosure also provide for a system for receiving temporal data generated by the x-ray detection device, and accurately tagging received image frames based on the temporal data.

18 Claims, 18 Drawing Sheets

(56) References Cited

U.S. PATENT DOCUMENTS

| | | | |
|---|---|---|---|
| 2013/0308827 A1* | 11/2013 | Dillavou | G06T 11/00 |
| | | | 382/107 |
| 2014/0270436 A1 | 9/2014 | Dascal et al. | |
| 2014/0276684 A1* | 9/2014 | Huennekens | A61B 17/320758 |
| | | | 606/7 |
| 2015/0023466 A1* | 1/2015 | Melman | A61B 6/542 |
| | | | 378/42 |
| 2015/0094564 A1* | 4/2015 | Tashman | A61B 6/563 |
| | | | 600/407 |
| 2015/0173697 A1* | 6/2015 | Parks | A61B 6/12 |
| | | | 600/301 |
| 2017/0039738 A1* | 2/2017 | Ziv | G01T 1/249 |
| 2017/0219501 A1* | 8/2017 | Yakimov | A61B 6/4208 |
| 2017/0245822 A1 | 8/2017 | Vaillant et al. | |
| 2018/0078226 A1* | 3/2018 | Helm | A61B 6/545 |
| 2019/0350546 A1* | 11/2019 | He | A61B 6/42 |
| 2020/0205769 A1* | 7/2020 | Kotian | A61B 6/542 |
| 2020/0286237 A1 | 9/2020 | Butler | |
| 2021/0137469 A1* | 5/2021 | Zhao | A61B 6/4452 |
| 2021/0244374 A1* | 8/2021 | Zhao | A61B 6/4241 |
| 2021/0369222 A1* | 12/2021 | Fontaine | A61B 6/5205 |
| 2022/0121854 A1* | 4/2022 | Bourn | G06F 16/7837 |

* cited by examiner ial Patent Application No. 63/271,524, filed
TEMPORAL DATA GENERATION WITH SCATTERED X-RAY RADIATION

CROSS-REFERENCE TO RELATED APPLICATIONS

This application claims the benefit of the filing date of U.S. Provisional Patent Application No. 63/271,524, filed Oct. 25, 2021, the disclosure of which is hereby incorporated herein by reference.

BACKGROUND

Catheterization laboratories include imaging equipment for taking x-ray photographs of cardiovascular systems of a patient, such as the heart or blood vessels of the patient, as part of an angiographic imaging procedure. A sequence of pulses of radiation is emitted from a beam source and directed towards the patient. A sequence of image frames can be generated using the sequence of pulses. The patient can also be injected with contrast dye, which can be used to highlight or emphasize at least some part of the patient's cardiovascular system in the image sequence. A computing device connected to the imaging equipment can display image frames on a display, and the image frames can be displayed in a looped playback. An operator can cause the imaging equipment to emit several sequences of pulses over a period of time, and the computing device can display image frames generated from each sequence on a display.

The computing device of the imaging equipment grabs and processes image frames as they appear as part of a received video stream or sequence of image frames. Frame grabbers are devices for capturing—or grabbing—image frames from a stream of images provided by an imaging device.

Optical coherence tomography (OCT) is an imaging technique with widespread applications in ophthalmology, cardiology, gastroenterology, and other fields of medicine and scientific study. OCT can be used in conjunction with various other imaging technologies, such as intravascular ultrasound (IVUS), angiography, fluoroscopy, and x-ray-based imaging. To perform imaging, an imaging probe can be mounted on a catheter and maneuvered through a point of interest, such as through a blood vessel of a patient.

BRIEF SUMMARY

Aspects of the disclosure provide for an x-ray detection device for detecting radiation scattered off a target during an imaging procedure and generating temporal data indicating the time of occurrence of a pulse of radiation emitted towards the target. The temporal data can be sent to a host device and used to timestamp images generated from the pulses of radiation. The host device may be connected to imaging equipment for imaging a patient, or may receive the images, for example, from a device in a catheterization laboratory. The x-ray detection device is portable and can be installed in a catheterization laboratory or other imaging environment, without occluding the beam source, to detect the occurrence of radiation, Aspects of the disclosure also provide for a system for receiving temporal data generated by the x-ray detection device, and accurately tagging received image frames based on the temporal data. With accurate real-time detection of radiation pulses based on detecting scattered radiation, angiographic image frames can be accurately tagged. Accurate real-time detection according to aspects of the disclosure can also improve co-registration processes with other image frames, including OCT images, as well as provide real-time validation of OCT pullbacks performed concurrently with x-ray imaging.

Images can be tagged more accurately as compared with tagging images based on a time a frame was grabbed by a host device from an image feed. Images can also be tagged more accurately as compared with tagging images based on timestamps provided by imaging equipment in catheterization laboratories, which may not be accurate or may not have clocks synchronized with a host processing device receiving the images. Real-time detection of radiation pulses for angiographic or x-ray imaging can also improve the workflow of an imaging procedure, by reducing or eliminating the need for user confirmation for the start or end of a sequence of radiation pulses during imaging.

An aspect of the disclosure provides for a system including: one or more processors configured to: receive, from an x-ray detection device, temporal data specifying a time of detection of scattered radiation from a radiation pulse emitted towards and at least partially reflected by a human or animal body; receive an image frame of a region of the human or animal body; and tag the image frame using the temporal data.

Aspects of the disclosure also include a computer-implemented method and computer-readable storage media storing instructions that when executed by one or more processors, causes the one or more processors to perform operations as described herein. In addition, aspects of the disclosure can include one or more of the following features. In some examples, aspects of the disclosure provide for all of the features, in combination.

The one or more processors are further configured to send the tagged image frame for display on a display device coupled to the one or more processors.

The one or more processors are further configured to: synchronize a host clock coupled to the one or more processors with a device clock of the x-ray detection device; and determine a video latency value, the video latency value corresponding to a length of time between receiving an image frame by the one or more processors, and a time of detection of scattered radiation from the radiation pulse.

The one or more processors are further configured to initiate synchronization or determination of the video latency value in response to receiving the temporal data or the image frame.

The one or more processors are further configured to: after the one or more processors calculate the video latency value, send a prompt for display indicating a start time for contrast injection and a pullback of an imaging probe inside a blood vessel of the human or animal body.

The image frame is an initial image frame in a sequence of image frames, the temporal data includes a sequence of digital words, each digital word indicating an instance of scattered radiation detected by the x-ray detection device, and each digital word tagged with a respective timestamp indicating the time of detection for the scattered radiation, wherein the initial image frame is tagged with an initial digital word in the sequence of digital words, and wherein the one or more processors are further configured to, for each image frame, identify a next image frame in the sequence based on a predetermined interval and a video latency value; tag the identified image frame with a timestamp of a next digital word in the sequence of digital words; and determine whether the end of the sequence of image frames has been reached.

The predetermined interval is based at least on a frame rate at which the sequence of image frames was generated.

The one or more processors are further configured to receive a respective video latency value for each received sequence of image frames.

The video latency value is based at least on a respective operating mode of an imaging system at which the sequence of image frames was generated.

To determine whether the end of the sequence of image frames has been reached, the one or more processors are configured to: determine that a period of time equal to the predetermined interval plus a predetermined delta value has passed since the last tagged image frame in the sequence of image frames.

The one or more processors are configured to communicate wirelessly with the x-ray detection device.

The one or more processors are further configured to determine one or both of a start time and a stop time for a sequence of radiation pulses, using at least the temporal data received from the x-ray detection device.

The image frame is part of a sequence of image frames; wherein the one or more processors are configured to receive the sequence of image frames; and wherein to tag the image frame of the sequence of image frames with the temporal data, the one or more processors are further configured to determine whether an image frame of the plurality of image frames was received at a time equal to the predetermined interval plus a video latency value after receiving a previous image frame in the sequence of image frames.

The one or more processors are configured to tag the image frame of the sequence of image frames while receiving respective temporal data for each of the plurality of radiation pulses.

The image frame is a first image frame; and wherein the one or more processors are further configured to: receive a second image frame; and generate data defining a co-registration between the second image frame and the first image frame, using at least the temporal data tagged to the first image frame.

The second image frame was generated according to a modality different from the first image frame.

The first image frame is an angiographic image of a portion of a cardiovascular system of the imaged human or animal body, and wherein the second image frame is an image frame of the portion of the cardiovascular system of the imaged human or animal body taken using optical coherence tomography.

Aspects of the disclosure provide for an x-ray detection device, the x-ray detection device including: a scintillator; a photodiode; and one or more processors configured to: receive, from the photodiode, an electrical signal corresponding to an occurrence of scattered radiation detected by the scintillator, wherein the scattered radiation includes radiation from a radiation pulse emitted towards and at least partially reflected by a human or animal body; generate, using at least the electrical signal, temporal data specifying a time of the occurrence of the scattered radiation detected by the scintillator; and send the temporal data to a computing device in communication with the x-ray detection device.

Aspects of the disclosure provide for a number of the following features, alone or in combination. In some examples, an x-ray detection device as described herein includes all of the following features, in combination.

The device is positioned to not occlude or partially occlude the radiation pulse as it is emitted towards the human or animal body.

The electrical signal is a first electrical signal, and wherein the one or more processors are further configured to: receive one or more second electrical signals, each second electrical signal corresponding to a respective occurrence of scattered radiation and send the temporal data to the computing device in communication with the x-ray detection device while receiving the one or more second electrical signals.

The x-ray detection device includes a housing and a clip attached to the housing, wherein the clip is formed to connect to an examination table of a catheterization laboratory.

The x-ray detection device is configured to detect the occurrence of the scattered radiation while positioned to not occlude or partially occlude the radiation pulse as it is emitted towards the human or animal body.

The one or more processors are further configured to: in response to receiving the electrical signal, sending a request to the computing device to synchronize a clock of the x-ray detection device with a clock connected to the computing device.

DETAILED DESCRIPTION

Overview

Figure 1A:
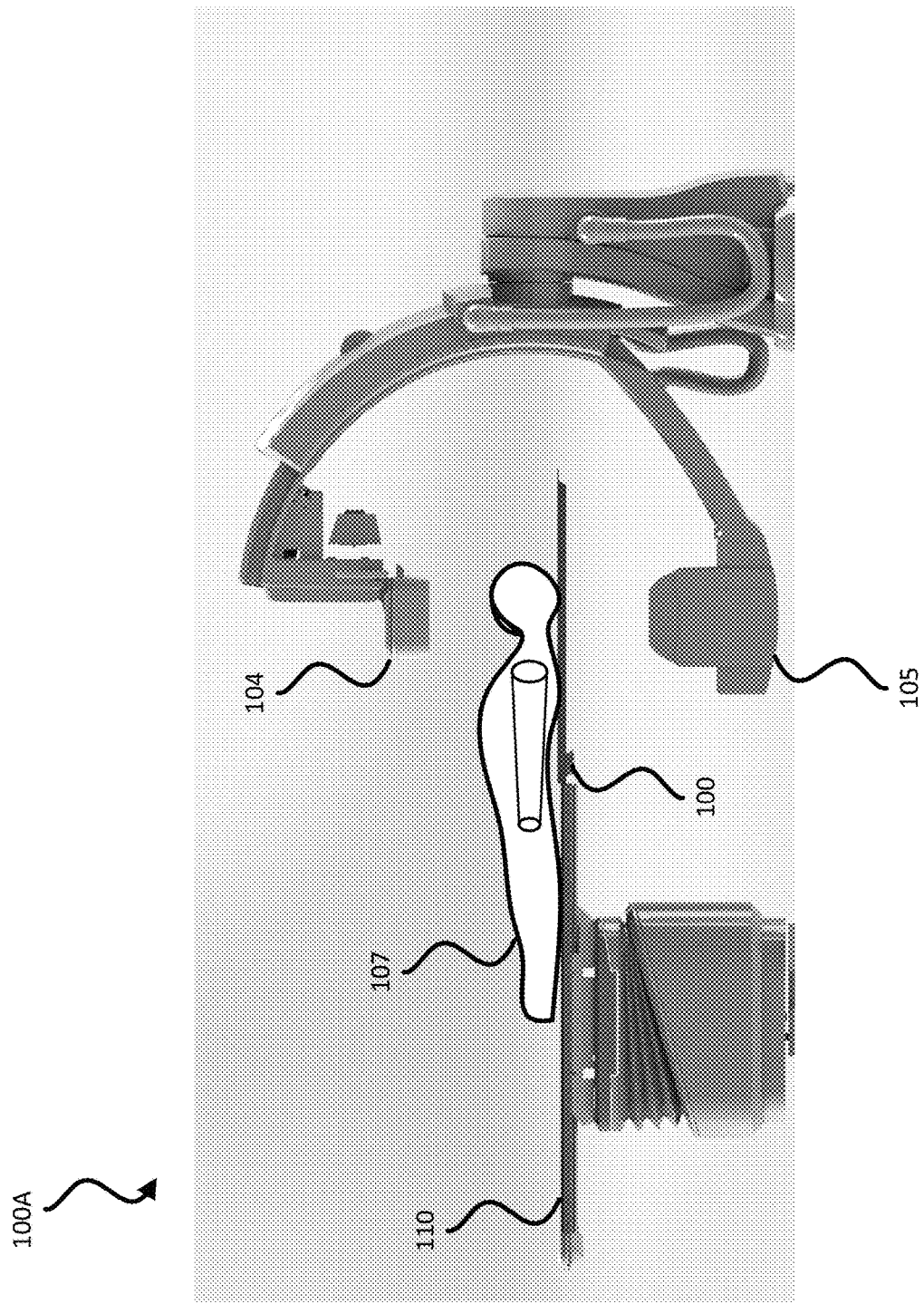
FIG. 1A is an illustration of a side view of imaging equipment coupled to an example x-ray detection device, according to aspects of the disclosure.

Aspects of the disclosure provide for an x-ray detection device for detecting scattered x-ray radiation from a patient undergoing a medical imaging procedure and providing temporal data for synchronizing timestamps for x-ray images with other medical image data. An x-ray detection device as described herein can interact with a host device controlling medical equipment. The medical equipment can be configured to perform a variety of medical image procedures using x-ray radiation, such as angiographic imaging. In some examples, the host device does not directly control the medical imaging equipment, but instead receives a sequence of images from a device, such as a computer in a catheterization lab, coupled to the medical imaging equipment. The x-ray detection device can be implemented to accurately provide temporal data specifying the occurrence of one or more pulses of detected radiation in real-time. The x-ray detection device can send the temporal data to the host device. The host device can at least partially implement companion software, such as a temporal data processing engine, for tagging angiographic images using the temporal data.

In this specification, a "cine acquisition" refers to the capture of a sequence of image frames—referred to as a "cine"—using pulses of x-ray radiation emitted at a predetermined interval. The host device identifies the first non-placeholder image frame in the cine, for example an image frame depicting a region of interest in a patient. The host device tags the initial image frame in the sequence with temporal data corresponding to the occurrence of the initial x-ray radiation pulse detected by the x-ray detection device. The host device identifies the second non-placeholder image frame with temporal data corresponding to the occurrence of a second x-ray radiation pulse, and so on.

The host device can synchronize the x-ray detection device and the host device, to reduce inconsistencies in timing caused by clock drift between the devices. The host device can identify subsequent image frames to tag based on a predetermined interval and predetermined video latency value between frames. The predetermined interval can be, for example, based on the frame rate of the imaging equipment. The video latency value can represent the amount of time between a radiation pulse emission and when the corresponding image frame is received by the host device.

Instead of measuring radiation directly from a beam source, the x-ray detection device is configured for detecting radiation scattered off of a target, such as a patient. In this way, the x-ray detection device can detect the occurrence of a cine acquisition in real-time, without occluding or partially occluding a beam source of the imaging equipment, potentially interfering with the quality of images in a corresponding cine.

The x-ray detection device is portable and can be implemented wirelessly, improving its versatility of interacting with a variety of different types, brands, and versions of medical imaging equipment. At the same time, the x-ray detection device and/or host device as described herein can automatically synchronize clocks between the x-ray detection device and the host device. In addition to tagging images, the temporal data generated by the x-ray detection device can be used to improve co-registration of images of different modalities taken by the medical imaging equipment, such as angiographic images co-registered with OCT images taken during a pullback procedure. Co-registration includes techniques for generating data for correlating characteristics of different images of a portion of a body, including blood vessels or tissue. For example, angiographic images of a blood vessel of a patient can be co-registered with OCT images taken through an imaging probe in the blood vessel at or near the same time. In other examples, images taken at different points in time can be co-registered.

The x-ray detection device provides real-time feedback of temporal data for each angiographic image captured by the imaging equipment, which can be used to automate workflows for various imaging procedures performed in the catheterization laboratory with the x-ray detection device as described herein. For example, with accurate temporal data, the host device with an installed temporal data processing engine can automatically prompt a user or operator when an OCT pullback performed concurrently with a cine acquisition is invalid or valid. Determining the validity of the OCT pullback can be based on its start and stop time within a cine acquisition. As another example, the host device can prompt the user or operator to begin adding a contrast dye to the patient during a cine acquisition.

By tagging image frames using the temporal data, a system including the x-ray detection device and one or more processors as described herein can prevent missing frames for tagging in a cine. The system can also prevent duplicating the same frame twice, which would otherwise occur in approaches relying on frame grabber technology or other similar approaches. As part of this detection, the system can determine whether an image frame is received during an on-going cine acquisition, to avoid tagging image frames not taken as part of a current cine acquisition with current temporal data. By contrast, devices relying on frame grabbers for timestamping image frames may duplicate or omit some image frames. Devices relying on frame grabbers may receive image frames from a looped playback on the display of the host device of old image frames displayed during a video playback loop but not captured as part of a current cine acquisition.

Example Systems

FIG. 1A is an illustration of a side view 100A of an imaging device 104 and an example x-ray detection device 100, according to aspects of the disclosure. The x-ray detection device 100 can be installed in a catheterization laboratory or any environment where imaging is done at least partially with x-rays. For example, the environment can be used for angiographic procedures, and also be equipped for performing OCT imaging procedures and any of a variety of other medical imaging procedures. Angiographic procedures can include imaging the target with and without contrast dye injection. The imaging device 104 can include a beam source 105 for x-rays angled and focused on a target 107, for example a human or animal body. X-ray images can be taken in combination with image frames generated using other modalities, such as OCT, IVUS, micro-OCT, and/or NIRS.

The beam source 105 emits one or more pulses of radiation in response to some input, e.g., a pedal press or other input by an operator of the imaging device 104. The x-ray detection device 100 can be clipped or placed proximate to the target 107 as described herein with reference to FIG. 1B. The x-ray detection device 100 can be configured to detect radiation as the radiation is emitted from the beam source 105 and scattered off of the target 107. The x-ray detection device 100 can be positioned so as to not occlude or partially occlude the beam source as radiation is pulsed to the target 107. As described herein with reference to FIGS. 2A-3B, the x-ray detection device 100 is configured to generate temporal data, such as timestamps or time tags, indicating when scattered radiation is detected by the device 100. The x-ray detection device 100 can send the temporal data specifying times at which radiation pulses are detected to a host device coupled to both the imaging device 104 and the x-ray detection device 100, as described herein with reference to FIG. 3B.

The host device, configured with a temporal data processing engine as described herein, can tag image frames taken using the temporal data. The x-ray detection device 100 can be configured to detect and generate temporal data for each pulse in real time. The x-ray detection device 100 can be wirelessly connected or connected to the temporal data processing engine installed on the host device, as described herein with reference to FIG. 3B.

The x-ray detection device 100 can be configured to determine the time of occurrence of an initial pulse of radiation and terminal pulse of radiation within a sequence of pulses emitted by the beam source 105. The x-ray detection device 100 can determine a start time of a sequence of pulses automatically through detection of the scattered radiation and does not require separate user input from an operator of the imaging device 104.

Figure 1B:
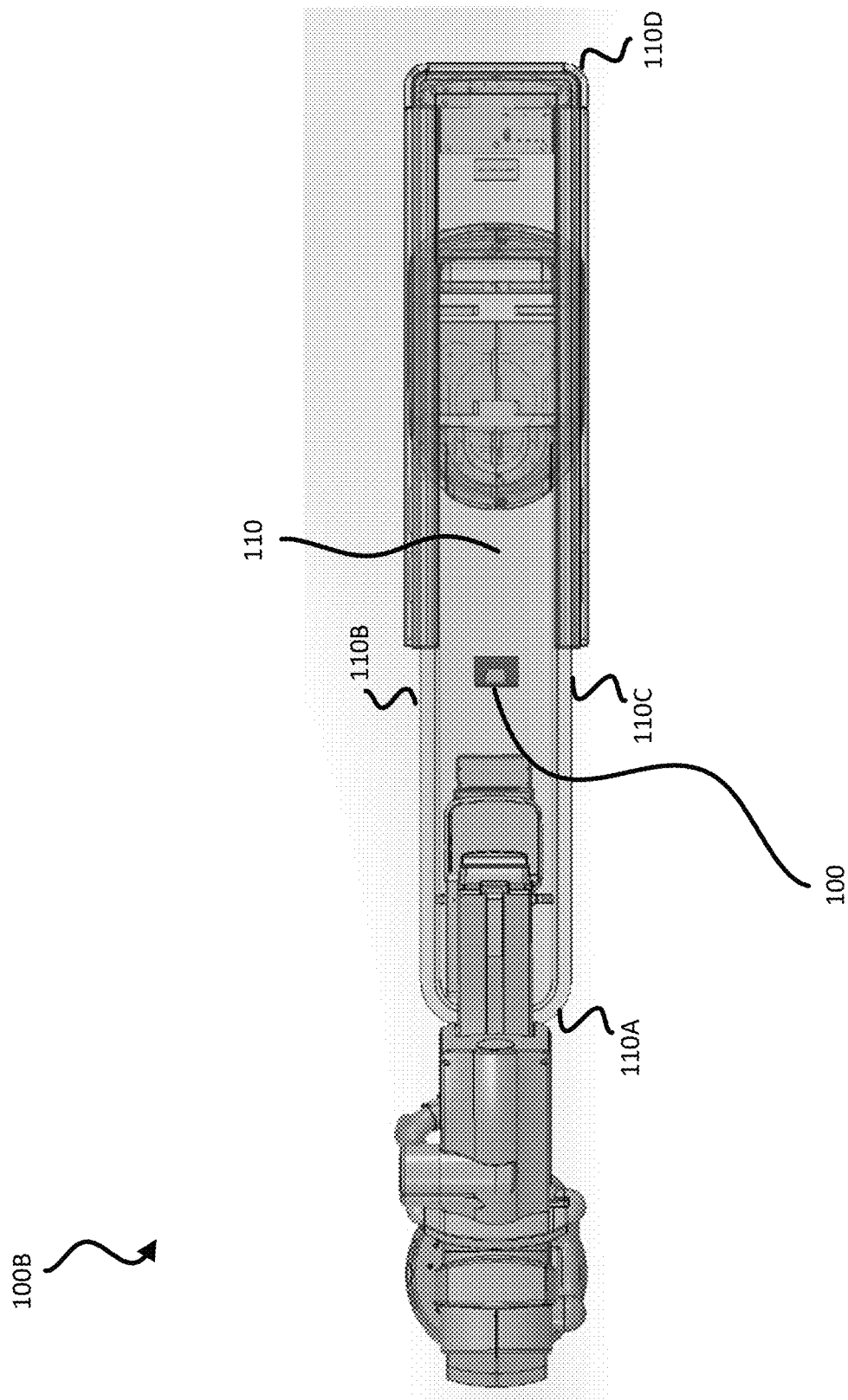
FIG. 1B is an illustration of a top-down view of the example x-ray detection device coupled to an examination table as shown in FIG. 1A.

FIG. 1B is an illustration of a top-down view 100B of the example x-ray detection device 100 coupled to an examination table 110 as shown in FIG. 1A. The x-ray detection device 100 can be positioned anywhere proximate to the target to receive scattered radiation emitted by the beam source 105. For example, the x-ray detection device 100 as shown in FIG. 1B is attached beneath the examination table 110. In other examples, the x-ray detection device 100 can be attached on the side of the examination table 110, for example on one side of the target 107.

Figure 1C:
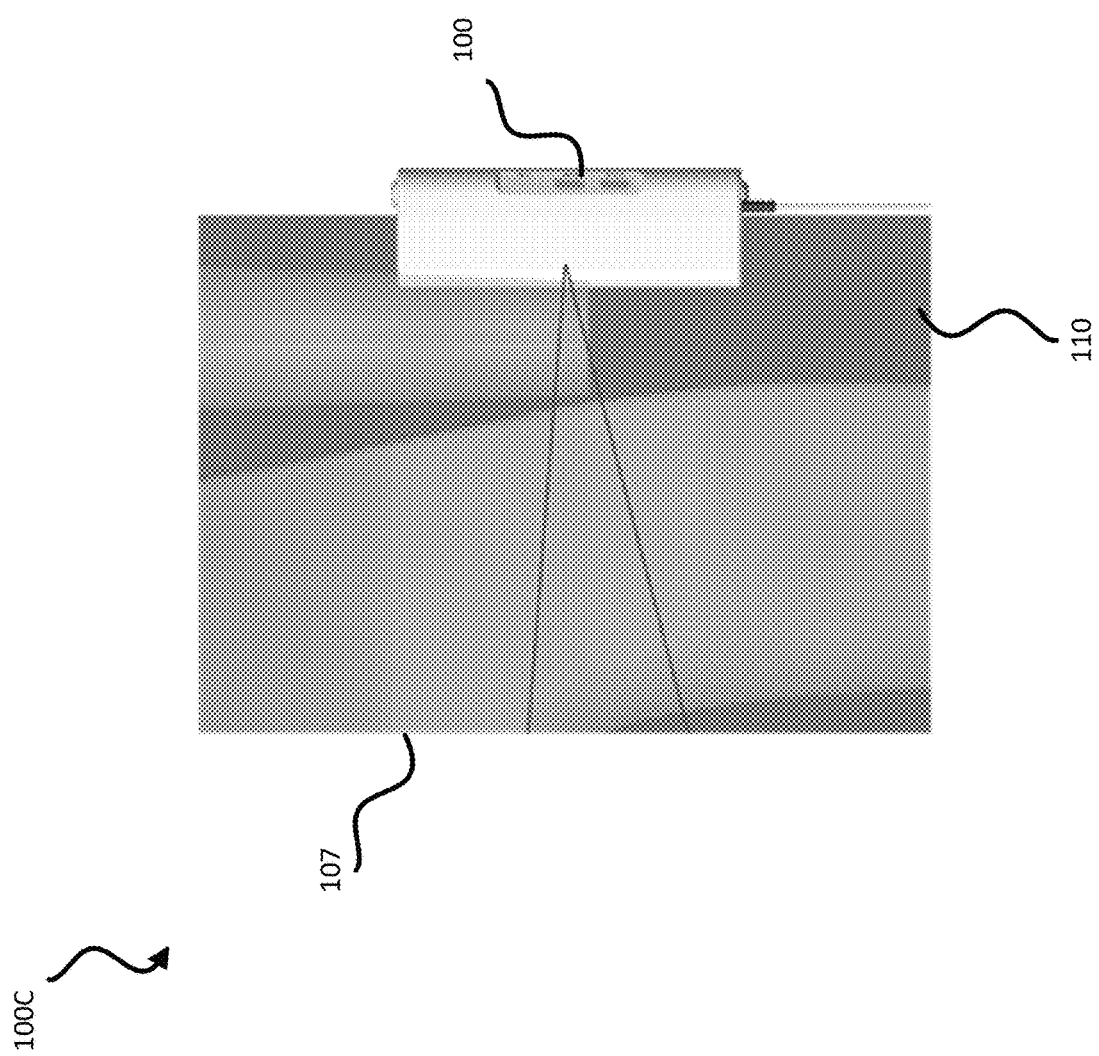
FIG. 1C is an illustration of a top-down view of the imaging equipment coupled to another example of the x-ray detection device mounted to the examination table.

As shown in FIG. 1B, examination table 110 has four edges, edge 110A, edge 110B, edge 110C, and edge 110D. In different examples, the x-ray detection device 100 can be placed at different distances relative to the target 107 when the target 107 is on the examination table 110. For example, if the x-ray detection device 100 is attached to the examination table 110, the x-ray detection device 100 can be placed approximately 75 centimeters from the edge of the examination table 110 closest to the head of the target 107, e.g., edge 110A of the examination table 110 as shown in FIG. 1C. As another example, the x-ray detection device 100 can be placed underneath the examination table 110 and in the middle between the lateral sides of the examination table 110. The x-ray detection device 100 can be placed approximately 82 centimeters from the edge of the examination table 110 closest to the head of the target 107, e.g., edge 110A as shown in FIG. 1B.

FIG. 1C is an illustration of a top-down view 100C of the imaging equipment coupled to another example of the x-ray detection device mounted to the examination table. The x-ray detection device 100 can be positioned on the side of the examination table 110 where an operator can interact with the imaging device 104 and/or host device (not shown).

The x-ray detection device 100 is configured to detect scattered radiation while the beam source 105 is angled and/or positioned in a variety of different manners relative to the target 107. For example, the x-ray detection device 100 is configured to detect radiation when the beam source 105 is angled according to any of a variety of different positions for angiographic imaging, including anterior-posterior (AP) projection, left anterior oblique (LAO) angulation, right anterior oblique (RAO) angulation, cranial angulation, and caudal angulation. Within each of the different positions, the x-ray detection device 100 is configured to detect scattered x-rays from the target 107 from a variety of different angles, including, for example, anterior-posterior (AP) projection with 0 degree caudal/cranial angle; AP projection with 30 degree cranial angle; 10 degree right angular oblique (RAO) projection with 30 degree cranial angle; 40 degree left angular oblique (LAO) projection with 20 degree caudal angle; 50 degree LAO projection with 30 degree cranial angle; 30 degree LAO projection with 20 degree cranial angle; 20 degree RAO projection with 20 degree caudal angle; AP projection with 30 degree caudal angle; and 30 degree RAO projection with 20 degree cranial angle.

The x-ray detection device 100 can detect radiation from any of a variety of different shapes and sizes for the imaging device 104 coupled to the beam source 105, including all clinically defined c-arm geometries that can vary for different laboratories or environments. As described herein with reference to FIGS. 2A-3A, the x-ray detection device 100 can be configured for low-power, low-profile, wireless operation, allowing the device to be installed in a variety of different environments. The x-ray detection device 100 can detect scattered radiation and does not require interfacing directly with imaging equipment of a laboratory or environment. Instead, the x-ray detection device 100 can wirelessly interface with a host device implementing a temporal data processing engine configured to receive and process temporal data from the x-ray detection device 100.

The x-ray detection device 100 can detect scattered radiation from pulses at different levels of strength. The beam source 105 may have different dosage levels, for example to adjust the strength of a pulse depending on, for example, if the target is a child, e.g., a lower dose, or an adult, e.g., a standard dose as clinically defined.

Figure 1D:
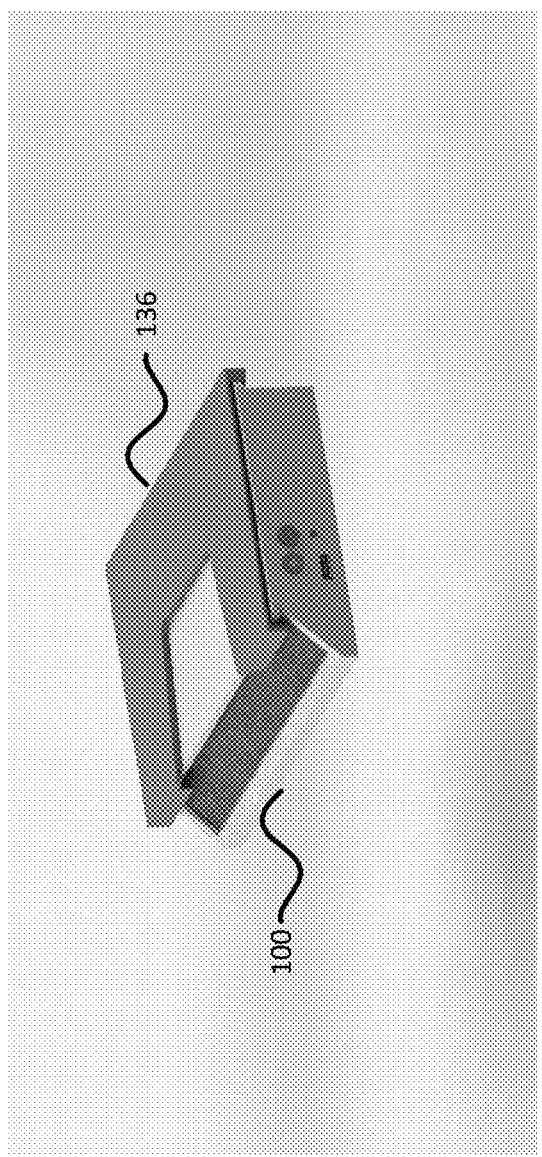
FIG. 1D is an illustration of a perspective view of the example x-ray detection device sheathed in an example table-mounted bracket.

FIG. 1D is an illustration of a perspective view 100D of the example x-ray detection device sheathed in an example table-mounted bracket. The table-mounted bracket 135 can be mounted underneath the examination table 110, for example through an adhesive, screws, etc. The table-mounted bracket 135 can be shaped so as to securely position the x-ray detection device 100 while sheathed in the bracket 135, but also allow the device 100 to be easily removed.

Figure 1E:
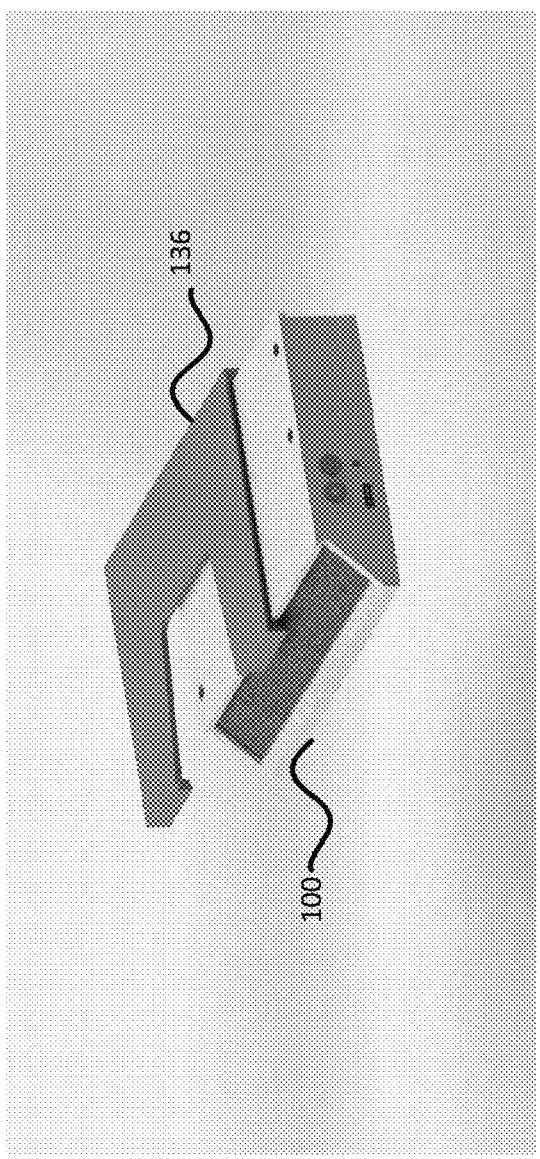
FIG. 1E is an illustration of a perspective view of the example x-ray detection device unsheathed in the example table-mounted bracket of FIG. 1D.

FIG. 1E is an illustration of a perspective view 100E of the example x-ray detection device unsheathed in the example table-mounted bracket of FIG. 1D. The x-ray detection device 100 may be removed from the table-mounted bracket 135.

Figures 1F, 1G:
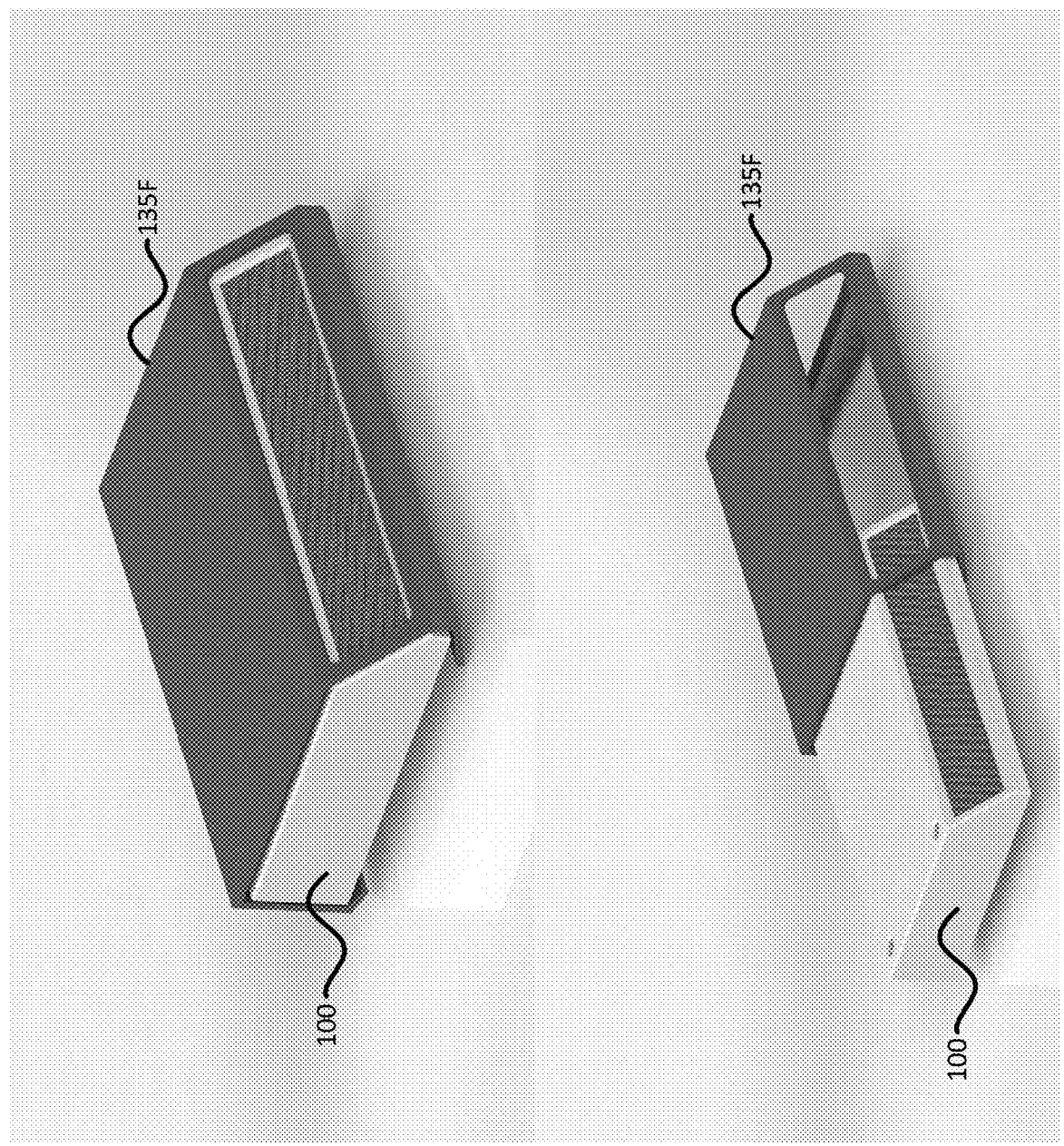
FIG. 1F is an illustration of a perspective view of the example x-ray detection device sheathed in another example table-mounted bracket.
FIG. 1G is an illustration of a perspective view of the example x-ray detection device unsheathed in the example table-mounted bracket of FIG. 1F.

FIG. 1F is an illustration of a perspective view 100F of the example x-ray detection device 100 sheathed in another example table-mounted bracket 136. FIG. 1G is an illustration of a perspective view 100G of the example x-ray detection device 100 unsheathed in the example table-mounted bracket 136 of FIG. 1F.

Figure 1H:
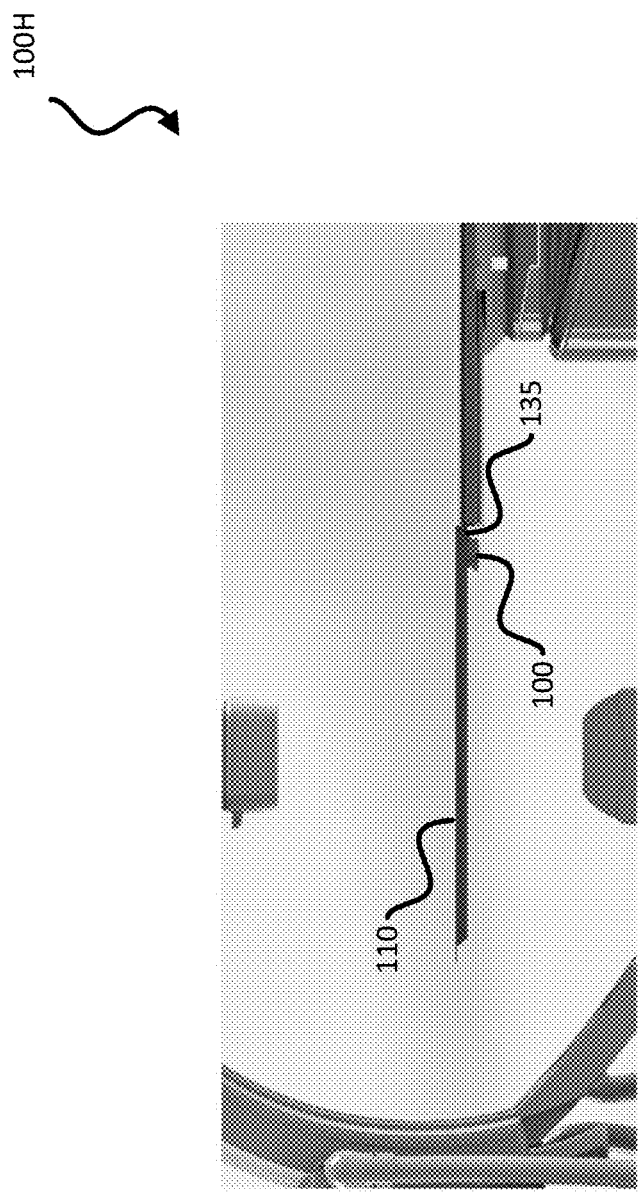
FIG. 1H is an illustration of a side view of the example x-ray detection device sheathed in a table-mounted bracket mounted to the examination table.

FIG. 1H is an illustration of a side view 100H of the example x-ray detection device 100 sheathed in the table-mounted bracket 135 mounted to the examination table 110. In some examples, the x-ray detection device 100 is mounted directly underneath the examination table 110 instead of being mounted on the edge of the table 110. In this way, the x-ray detection device 100 can be placed so as to not be accidentally bumped or disrupted by an operator, by being positioned in an otherwise unused space under the table 110.

Figure 2A:
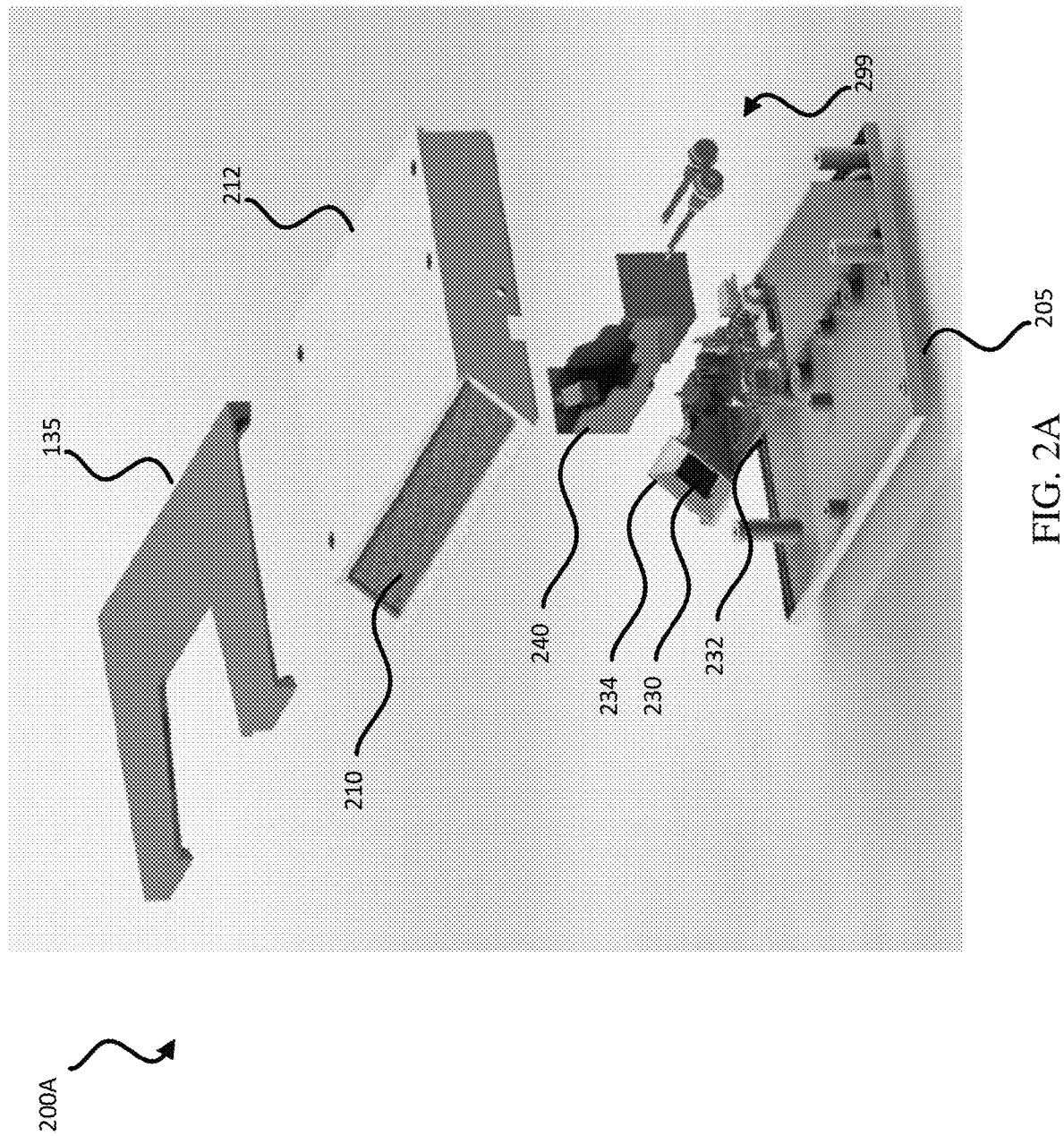
FIG. 2A is an illustration of a first exploded view of the example x-ray detection device.

FIG. 2A is an illustration of a first exploded view 200A of the example x-ray detection device 100. The x-ray detection device 100 is shown in an exploded view, including a housing 205, a control board 232, battery chamber 240, photodiode chamber 230, photodiode 234, the table-mounted bracket 135, a control board cover 212, and indicators 299. The housing 205 and the control board cover 212 can be made from any material conducive for housing a scintillator or other device for transferring x-ray radiation, for example a plastic or a carbon-based material. The housing 205 can be shaped to fit a variety of surfaces, for example edges of examination tables of a catheterization laboratory or other imaging environment. In some examples, the housing 205 can include straps, belts, adhesive strips, suction cups, etc., for securing the x-ray detection device 100 to a surface, while also allowing for the x-ray detection device 100 to be easily removed and placed in a different position as necessary.

The device 100 can include a control panel 210. The control panel 210 can include one or more user-interactable controls, including buttons, switches, knobs, etc., for controlling the operation of the x-ray detection device 100. For example, the control panel 210 can include controls for powering the x-ray detection device 100 on or off, and/or elements for providing a status of a battery charge level for a battery powering the x-ray detection device 100.

Indicators 299 may include light indicators, such as LEDs, for indicating whether the device 100 is operating and/or has passed a built-in operation test. In some examples, the device 100 can include additional indicators, such as indicators for the remaining battery life of the device 100. The batteries themselves can be rechargeable or single-use and coupled to the indicators 299 to pass information indicating whether the batteries should be replaced or recharged. The indicators 299, in some examples, can also indicate whether the x-ray detection device 100 is connected to a consistent source of external power, versus operating over battery.

Figure 2B:
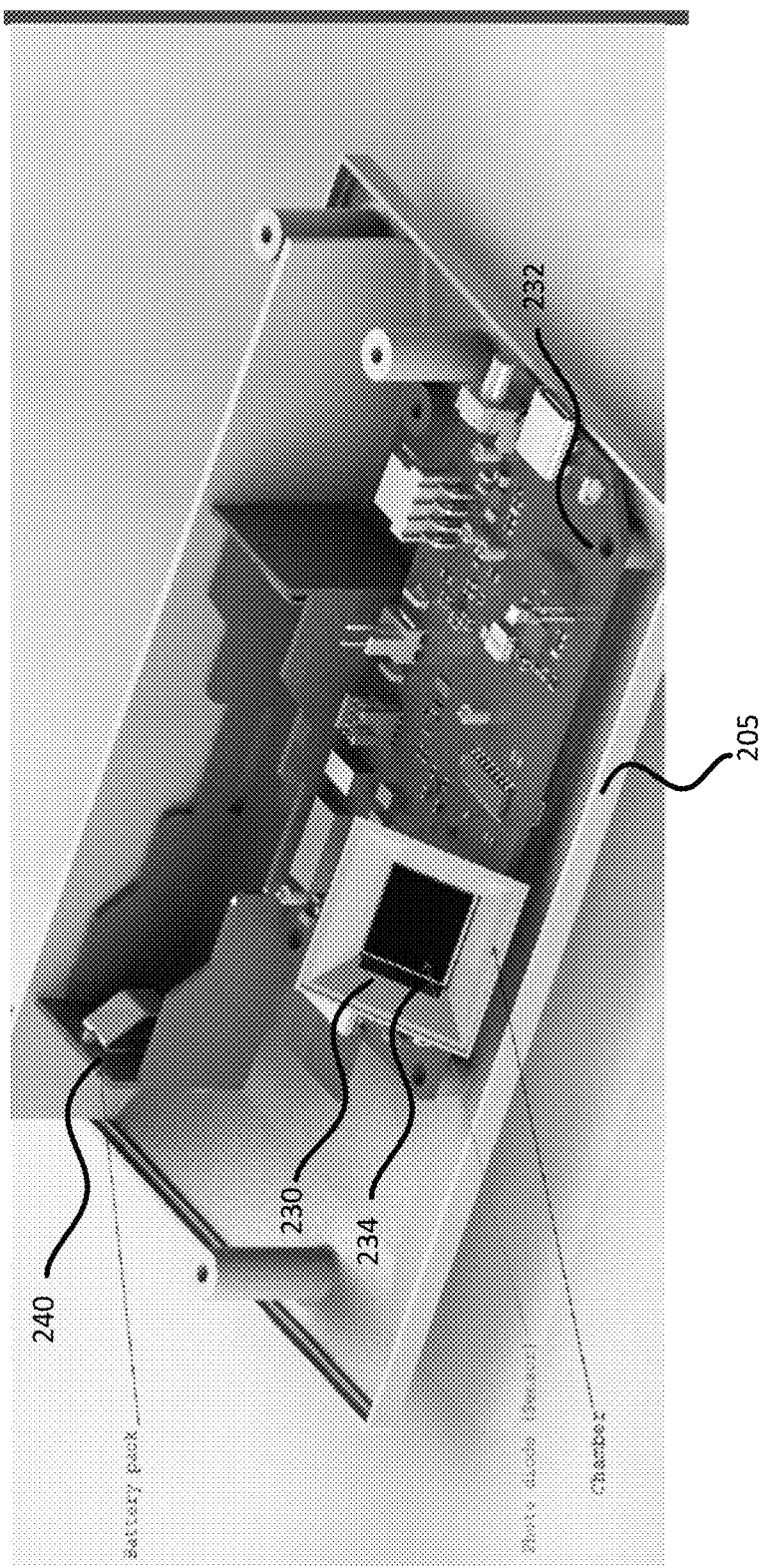
FIG. 2B is an illustration of a second exploded view of the example x-ray detection device.

FIG. 2B is an illustration of a second exploded view 200B of the example x-ray detection device 100. The control board 232 can be configured to sync the device 100 to a host device, as described herein with reference to FIG. 5. The x-ray detection device 100 can also include a wired connection port 235, which can be adapted for receiving cables according to one of a variety of different specifications, for example USB, including USB-C.

The battery chamber 240 can house one or more batteries for powering the device 100. In some examples, the x-ray detection device 100 is configured to receive power through a cable or other external source of power, in addition to or as an alternative to battery power. The batteries can be any one of a variety of different types of battery for powering portable devices, such lithium batteries. In some examples, the x-ray detection device 100 is powered by two 3.6-volt lithium batteries. The batteries can be single-use or rechargeable. The housing 205 can include a removable panel for accessing the inner components of the device 100. The removable panel can be made from the same or similar materials as the housing 205, for example carbon-based materials which will not inhibit the detection of scattered radiation by the x-ray detection device 100 during operation.

Figure 3A:
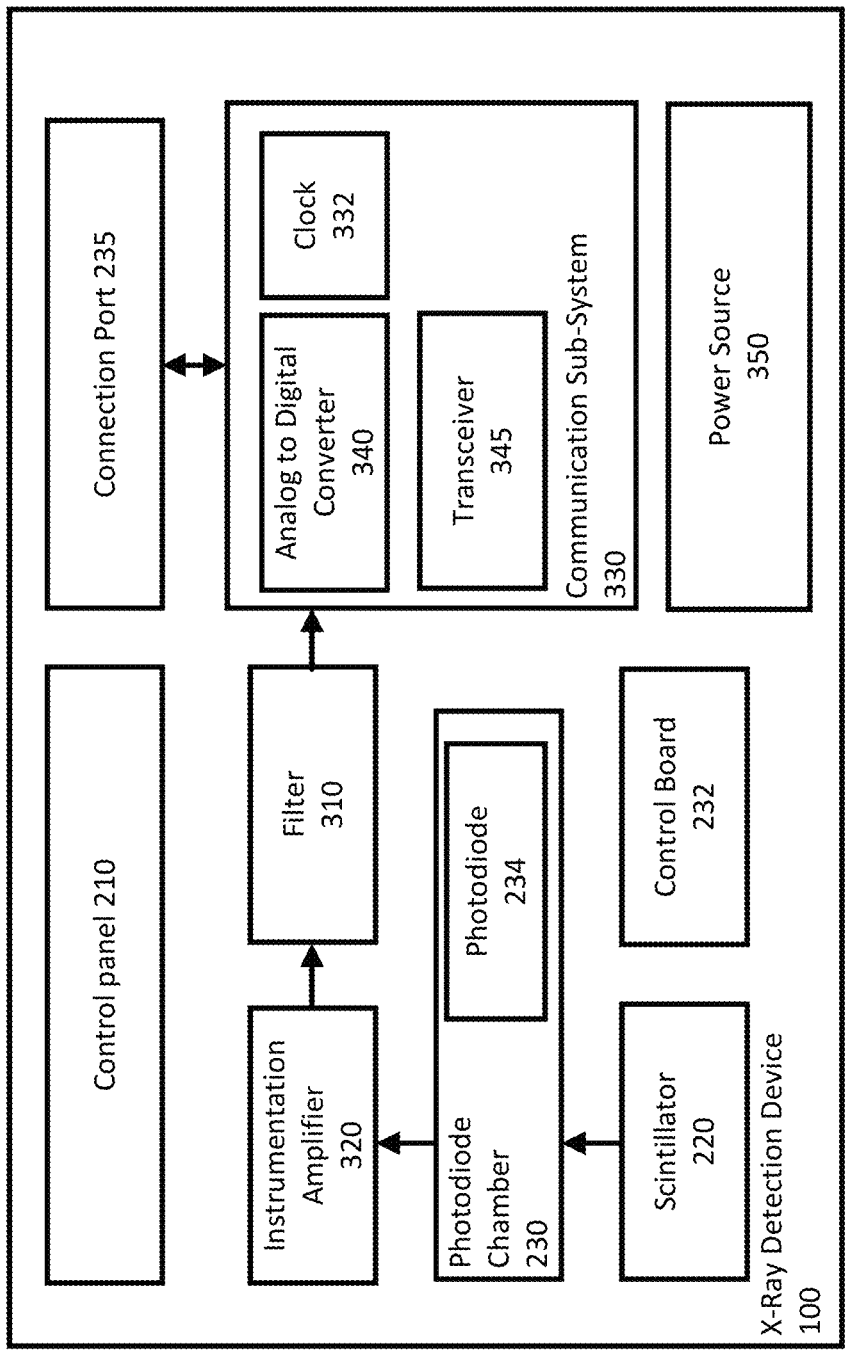
FIG. 3A is a block diagram of the example x-ray detection device, according to aspects of the disclosure.

FIG. 3A is a block diagram of the example x-ray detection device 100, according to aspects of the disclosure. The block diagram includes the scintillator 220, the photodiode chamber 230 with the photodiode 234, the control panel 210, the control board 232, and the connection port 235, as described herein with reference to FIGS. 2A-2B. Power source 350 can be a battery or source of wired power, as described herein with reference to FIG. 2B.

The scintillator 220 is configured to convert the scattered radiation into visible light. The photodiode 234 receives the visible light from the scintillator 220 and converts the light into an electrical signal. The photodiode chamber 230 can be made of an opaque material for blocking light from reaching the photodiode 234, except for the light from the scintillator 220. The photodiode chamber 120 can concentrate light from the scintillator 220 towards the photodiode 234. The x-ray detection device 100 passes the electrical signal through a filter 310. The filter 310 can be implemented using one or more circuits configured to receive, as input, the electrical signal, and generate, as output, a filtered version of the electrical signal. For example, the filter 310 can be a passive low-pass filter, configured to remove signals higher than a predetermined frequency, for example 154 MHz. The frequency can be predetermined based on an identification of a frequency of scattered radiation converted into visible light.

The x-ray detection device 100 passes the filtered electrical signal through an instrumentation amplifier 320. The instrumentation amplifier 320 can include one or more circuits configured to amplify the filtered signal, for example with a gain of 805V/V. The x-ray detection device 100 passes the amplified and filtered electrical signal to a communication sub-system 330. The communication sub-system 330 can be, for example, a system-on-a-chip (SoC) including a microcontroller or other type of processor and be configured for communicating data to a host device described herein with reference to FIG. 3B. The communication sub-system 330 can include an analog-to-digital converter (ADC) 340, which can be implemented as one or more circuits configured to receive the amplified and filtered electrical signal from the instrumentation amplifier 320, and to generate a digital signal from the electrical signal. The digital signal can be a digital word of a predefined length.

Figure 3B:
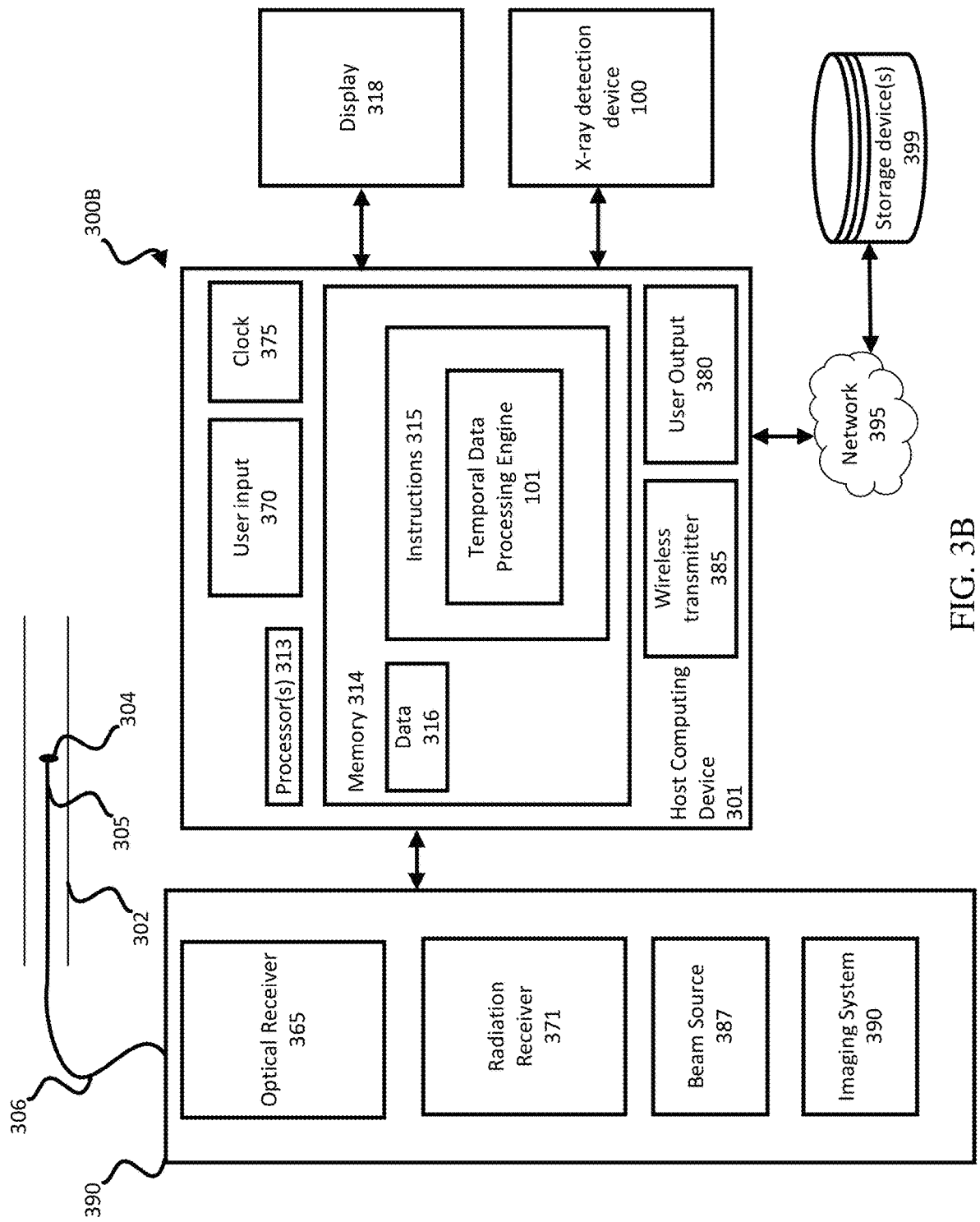
FIG. 3B is a block diagram of an imaging environment including the x-ray detection device and a temporal data processing engine implemented on a host computing device.

The communication sub-system 330 is configured to wirelessly communicate the generated temporal data to a host device, as described herein with reference to FIG. 3B. The sub-system 330 can implement any of a variety of different wireless protocols over short- or long-range connections. Examples include 2.402 GHz to 2.480 GHz (commonly associated with the Bluetooth® standard), 2.4 GHz and 5 GHz (commonly associated with the Wi-Fi® communication protocol); or with a variety of communication standards, such as the LTE® standard for wireless broadband communication. As part of implementing any of a variety of different wireless protocols, the communication sub-system 330 can include a transceiver 345 for receiving and sending data according to the wireless protocol. The communication sub-system 330 can also be configured for wired communication between the x-ray detection device 100 and a host device, for example through USB or various types of Ethernet connection. The x-ray detection device 100 can be configured to receive updates to one or more components, such as the communication sub-system 330, through a wired or wireless interface. Update data can be provided by the host device or another device coupled to the x-ray detection device 100.

The x-ray detection device 100 can include a number of features for improving a signal-to-noise ratio in received signals to the device 100. In some examples, the x-ray detection device includes a passive low pass filter and a single amplifier, which can help to reduce noise received by the device 100. Instead of being placed directly on the photodiode, in some examples, the scintillator 220 is placed on top of the photodiode chamber 230, to improve operation of the scintillator 220. The photodiode chamber 230 can in some examples be coated with a metal-colored internal coating to assist in directing the light from the scintillator 220 towards the photodiode 234.

The communication sub-system 330 is configured to identify valid x-ray radiation pulses detected by the x-ray detection device 100. For example, the sub-system 330 can identify an x-ray pulse based on the strength of scattered radiation detected by the device 100. The sub-system 330 can be configured with a predetermined range of radiation strengths capturing the strength of radiation when scattered off of the target 107. The exact range of detected strength can vary from implementation-to-implementation, according to a variety of factors. Some factors include the intended position of the x-ray detection device 100, and the strength and/or angle of the beam source 105.

The communication sub-system 330 is configured to generate temporal data corresponding to the time of detection of scattered radiation. The sub-system 330 can generate the temporal data as one or more tagged digital words. Each digital word can indicate an instance of scattered radiation detected by the x-ray detection device 100, and the tag to the digital word indicates the time of detection for the scattered radiation. The x-ray detection device 100 can tag a digital word representing detected scattered radiation within a small-time frame, such as 1 millisecond of the time at which the corresponding radiation pulse from the beam source 105 was actually emitted. The configuration of the x-ray detection device 100 provides for this reduced latency between pulse and temporal data generation, at least in part by its design as a low-power device, as well as by the flexibility of its design allowing for the device 100 to be positioned proximate to a beam source without obscuring the source itself.

The temporal data can represent the time of detection in any format, e.g., with data corresponding to the time of day in hours, minutes, and seconds. In some examples, the temporal data can also include higher levels of temporal precision, for example representing the time of detection within a range of milliseconds.

The communication sub-system 330 can include circuitry for maintaining an internal clock 332. The sub-system 330 can generate temporal data based on the time of the clock 332 for the sub-system 330 at the time of receiving a digital word. The x-ray detection device 100 and/or the host device is configured to synchronize the clock 332 with a clock 375 for the host device, as described herein with reference to FIG. 6. The synchronization can be done before each cine acquisition, to reduce the effects of clock drift that may occur between one or both of the clocks of the x-ray detection device 100 and the host device.

Synchronization between the clocks of the host device and the x-ray detection device can be performed by computing a communication latency value in transmitting a synchronization command from the host device and the x-ray detection device 100. The x-ray detection device can be positioned freely and does not require wires or cables that can potentially interfere with the imaging environment and/or an operator's use of the imaging environment during an imaging procedure. Computing latency automatically can help to prevent the wireless interface between the devices from interfering with the accuracy of tagging image frames generated during a cine acquisition. The latency value computed can be used to synchronize the clocks of the x-ray detection device and the host device.

FIG. 3B is a block diagram of an imaging environment 300B including the x-ray detection device 100 and a temporal data processing engine 101 implemented on a host computing device 301. The host computing device ("host device") 301 can include one or more processors configured for receiving signals from various types of imaging devices. The host device 301 can process the signals to generate one or more image frames or other visual data corresponding to the received signals.

The host device 301 can include a wireless transmitter 385 for communicating data to-and-from the x-ray detection device 100. In some examples, the wireless transmitter 385 can be connected to the host device 301 through a USB or other bus interface, as part of a peripheral device connected to the host device 301. In other examples, the host device 301 includes an integrated wireless transmitter, for example implemented as one or more circuits on a control board connecting other components of the host device, such as the processor(s) 313 and the memory 314. In other examples, the host device can be connected to an external device, such as a USB drive, configured to communicate data between the x-ray detection device 100 and the host device 301.

The host device 301 can include a user input 370. The user input 370 can include any appropriate mechanism or technique for receiving input from a user, such as keyboard, mouse, mechanical actuators, soft actuators, touchscreens, microphones, and sensors.

Figure 5:
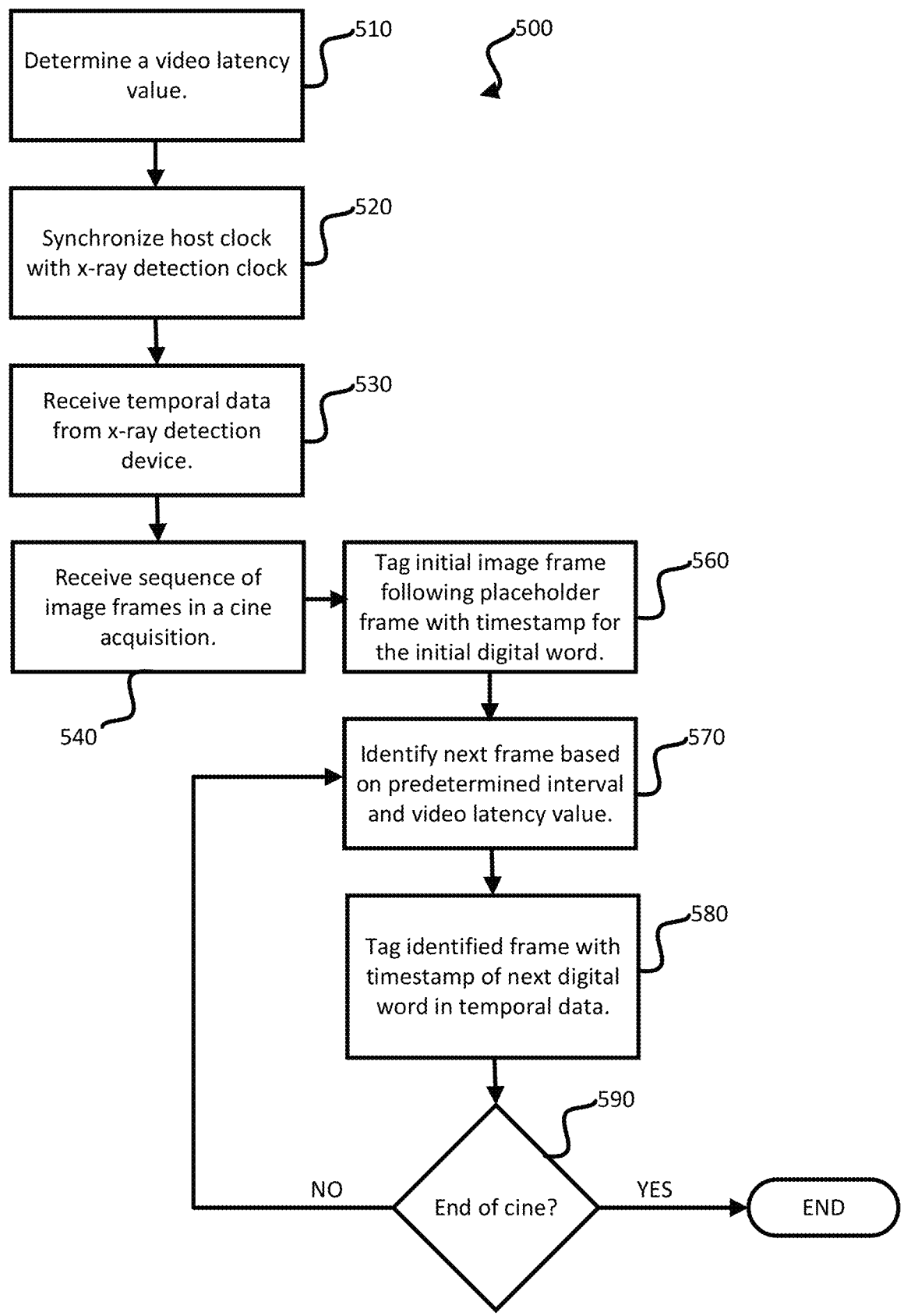
FIG. 5 is a flowchart of an example process for tagging x-ray images with temporal data, according to aspects of the disclosure.

The temporal data processing engine 101 is configured to tag received image frames with temporal data received from the x-ray detection device 100, for example as described herein with reference to FIG. 5. The engine 101 can also perform synchronization between the clocks 332, 375 of the x-ray detection device 100 and the host device 301. In some examples, the processing engine 101 can also be configured to use received temporal data from the x-ray detection device 100 to determine the start/stop time of a cine acquisition. The processing engine 101 can validate the correct start/stop time of an OCT pullback taken in parallel with the cine acquisition.

The host device 301 can receive image frames from an imaging system 390. The imaging system 390 can include an optical receiver 365, a radiation receiver 371, a beam source 387, and an imaging computing device 399. The imaging system 390 can be implemented as part of a catheterization laboratory and be configured to receive and process signals for generating image frames. For example, the imaging computing device 399 can be configured to receive radiation data from a radiation receiver 371. The radiation receiver 371 receives one or more pulses of radiation emitted from a beam source 387 and passed through a target, such as the body of a patient. The radiation receiver 371 can be part of an x-ray imaging device, for example the imaging device 104 of FIG. 1A. The imaging computing device 399 can be configured to generate x-ray image data from the received radiation data, and provide the x-ray images for display, for example on display 318.

The imaging computing device 399 can be configured to receive an image from an imaging device 305 having an imaging probe 304. The imaging probe 304 may be an OCT probe and/or an IVUS catheter, as examples. While the examples provided herein refer to an OCT probe, the use of an OCT probe is not intended to be limiting. An IVUS catheter may be used in conjunction with or instead of the OCT probe. A guidewire, not shown, may be used to introduce the probe 304 into a blood vessel 302, for example a blood vessel of the target 107. The probe 304 may be introduced and pulled back along a length of a lumen of the blood vessel 302 while collecting data, for example as a sequence of image frames. According to some examples, the probe 304 may be held stationary during a pullback such that a plurality of scans for OCT and/or IVUS data sets may be collected. The data sets, or frames of image data, may be used to identify fibrotic caps for lipid pools and other regions of interest.

The probe 304 may be connected to the imaging system 399 through an optical fiber 306. The imaging system 390 may include a light source, such as a laser, an interferometer having a sample arm and a reference arm, various optical paths, a clock generator, photodiodes, and other OCT and/or IVUS components. The probe 304 may be connected to an optical receiver 365. According to some examples, the optical receiver 365 may be a balanced photodiode-based system. The optical receiver 365 may be configured to receive light collected by the probe 304.

The imaging computing device 399 can receive the signal data received by the imaging system 390 and generate one or more image frames. The host device 301 is configured to receive the image frames from the imaging system 390. In some examples, the host device 301, as part of receiving one or more image frames, is configured to use the imaging system 390 to generate the image frames, for example by receiving and processing signals from the optical receiver 365.

The temporal data processing engine 101 can be implemented on one or more devices having one or more processors in one or more locations, such as in the host device 301. The host device 301 can be communicatively coupled to one or more storage devices 399 over a network 395. The storage device(s) 399 can be a combination of volatile and non-volatile memory and can be at the same or different physical locations as the host device 301 and/or x-ray detection device 100. For example, the storage device(s) 399 can include any type of non-transitory computer readable medium capable of storing information, such as a hard-drive, solid state drive, tape drive, optical storage, memory card, ROM, RAM, DVD, CD-ROM, write-capable, and read-only memories.

The host device 301 can include one or more processors 313 and memory 314. The memory 314 can store information accessible by the processor(s) 313, including instructions 315 that can be executed by the processor(s) 313. The memory 314 can also include data 316 that can be retrieved, manipulated, or stored by the processor(s) 313. The memory 314 can be a type of non-transitory computer readable medium capable of storing information accessible by the processor(s) 313, such as volatile and non-volatile memory. The processor(s) 313 can include one or more central processing units (CPUs), graphic processing units (GPUs), field-programmable gate arrays (FPGAs), and/or application-specific integrated circuits (ASICs).

The instructions 315 can include one or more instructions that when executed by the processor(s) 313, causes the one or more processors to perform actions defined by the instructions. The instructions 315 can be stored in object code format for direct processing by the processor(s) 313, or in other formats including interpretable scripts or collections of independent source code modules that are interpreted on demand or compiled in advance. The instructions 315 can include instructions for implementing the temporal data processing engine 101 consistent with aspects of this disclosure. The temporal data processing engine 101 can be executed using the processor(s) 313, and/or using other processors remotely located from the host device 301.

The data 316 can be retrieved, stored, or modified by the processor(s) 313 in accordance with the instructions 315. The data 316 can be stored in computer registers, in a relational or non-relational database as a table having a plurality of different fields and records, or as JSON, YAML, proto, or XML documents. The data 316 can also be formatted in a computer-readable format such as, but not limited to, binary values, ASCII or Unicode. Moreover, the data 316 can include information sufficient to identify relevant information, such as numbers, descriptive text, proprietary codes, pointers, references to data stored in other memories, including other network locations, or information that is used by a function to calculate relevant data.

The host device 301 can be configured to display at least a portion of the received data on a display implemented as part of the user output 380. The user output 380 can also be used for displaying an interface for the host device 301 on the display 318. The user output 380 can alternatively or additionally include one or more speakers, transducers or other audio outputs, a haptic interface or other tactile feedback that provides non-visual and non-audible information to a user of the host device 301.

The display 318 can display a video sequence including current and past cines. For example, the video sequence can be a loop of image frames. An image frame in the loop can be an image frame part of a current cine, e.g., an image captured as part of an ongoing cine acquisition. An image frame may also be a placeholder frame, e.g., a black or static frame, separating frames of different cines in the sequence. An image frame may also be from a previously acquired cine.

Although FIG. 3B illustrates the processor(s) 313 and the memory 314 as being within the host device 301, components described in this specification, including the processor(s) 313 and the memory 314, can include multiple processors and memories that can operate in different physical locations and not within the same computing device. For example, some of the instructions 315 and the data 316 can be stored on a removable SD card and others within a read-only computer chip. Some or all of the instructions and data can be stored in a location physically remote from, yet still accessible by, the processor(s) 313. Similarly, the processor(s) 313 can include a collection of processors that can perform concurrent and/or sequential operation. The host device 301 can each include one or more internal clocks providing timing information, which can be used for time measurement for operations and programs run by the host device 301. In some examples, the host device 301 is physically remote from imaging equipment from which image data or image frames are received. The host device 301 can be configured to receive temporal data, image frames, and/or other data over the network 395.

The host device 301 can be capable of direct and indirect communication with one or more other devices over the network 395. The host device 301 can set up listening sockets that may accept an initiating connection for sending and receiving information. The network 395 itself can include various configurations and protocols including the Internet, World Wide Web, intranets, virtual private networks, wide area networks, local networks, and private networks using communication protocols proprietary to one or more companies. The network 395 can support a variety of short- and long-range connections. The short- and long-range connections may be made over different bandwidths, such as 2.402 GHz to 2.480 GHz (commonly associated with the Bluetooth® standard), 2.4 GHz and 5 GHz (commonly associated with the Wi-Fi® communication protocol); or with a variety of communication standards, such as the LTE® standard for wireless broadband communication. The network 395, in addition or alternatively, can also support wired connections between the host device 301, the x-ray detection device 100, and/or other computing devices, including over various types of Ethernet connection.

Although a single host device 301 and x-ray detection device 100 are shown in FIG. 3B, it is understood that aspects of the disclosure can be implemented according to a variety of different configurations and quantities of devices, including paradigms for sequential or parallel processing, or over a distributed network of multiple devices. In some implementations, aspects of the disclosure can be performed on a single device, and any combination thereof.

Figure 4:
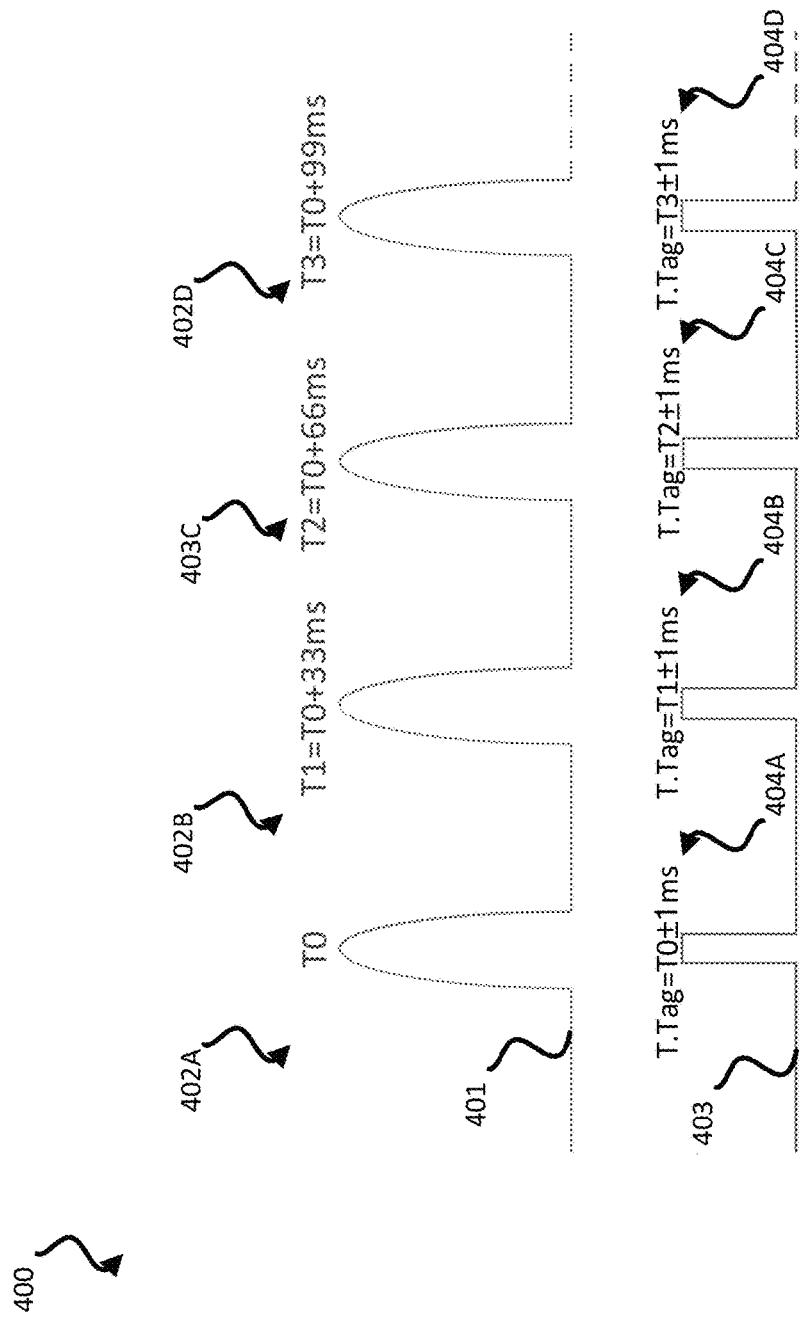
FIG. 4 is a chart showing x-ray pulses and temporal data associated with each pulse using the example x-ray detection device.

FIG. 4 is a chart 400 showing x-ray pulses and temporal data associated with each pulse using the example x-ray detection device. Line 401 shows detected radiation pulses from scattered radiation by the x-ray detection device, as described herein. The line 401 shows four occurrences of detected radiation, shown by peaks 402A-D at times $T_0$, $T_1$, $T_2$, and $T_3$. Each time $T_{0-3}$ is separated by a predetermined interval, in this example 33 milliseconds. The interval is based at least on a frame rate of a cine generated from the sequence of pulses emitted by a beam source between $T_0$ and $T_3$. For higher frame rates in a generated cine, the beam source can emit more pulses. For lower frame rates in the generated cine, the beam source can emit fewer pulses.

Line 403 shows the corresponding x-ray pulse detection events generated by the x-ray detection device, in response to detecting the occurrence of scattered radiation at times $T_0$ through $T_3$. Each event is tagged with a corresponding timestamp, shown in FIG. 4 as tags 404A-D.

Example Methods

FIG. 5 is a flowchart of an example process 500 for tagging x-ray images with temporal data, according to aspects of the disclosure. For example, a host device having one or more processors can perform the process 500.

The host device determines a video latency value, according to block 510. Video latency refers to the time between the first x-ray radiation pulse emitted for a new cine acquisition to the generation of a corresponding image frame. The video latency value can vary, for example based on the mode the beam source is operating in, such as low dose or high dose mode. Other factors that can affect the video latency value can include the hardware of the host device and/or the imaging system generating the image frame, as well as the connection between the host device and the imaging device. The host device can determine the video latency before each cine acquisition.

The host device synchronizes a clock for the host device with the clock of the x-ray detection device, according to block 520. Clocks over time may drift or deviate from a correct time for a variety of reasons, including the precision of the clock and the hardware or software implementing the clock on a respective device. To synchronize with the x-ray detection device, the host device can send data to the x-ray detection device and measure the time to receive a response from the x-ray detection device. The data sent to the x-ray detection device can be, for example, of the same size as the temporal data sent by the x-ray detection device during detection of scattered radiation. While the calculation can be performed once, in some examples, the host device repeats calculation of a communication latency value multiple times and can average out calculated latency values to generate a final average communication latency value.

In some examples, the x-ray detection device is synchronized with the host device in response to user input, for example through a button on a control panel for the x-ray detection device. In other examples, the x-ray detection device sends a request in response to detecting scattered radiation after a predetermined period of time. For example, the x-ray detection device can send a request for each cine acquisition detected by the device. The predetermined period of time can be a length of time that is longer than the maximum delay between pulses of radiation in a sequence of radiation pulses emitted as part of a cine acquisition. In other examples, the host device synchronizes with the x-ray detection device upon receiving an image frame for tagging. In some examples, the x-ray detection device can synchronize the clocks according to block 520, in addition or as an alternative to the host device.

The host device receives temporal data from an x-ray detection device, according to block 530. For example, the x-ray detection device can generate a sequence of tagged digital words as temporal data. Each digital word corresponds to an occurrence of detected scattered radiation, and the tag on the digital word represents the time the pulse of radiation corresponding to the scattered radiation occurred. The sequence of digital words can be streamed into the host device, or in some examples received all at once after the cine acquisition is complete.

The host device receives a sequence of image frames, according to block 540. The image frames are displayed on a display connected to the host device. For example, the image frames can be part of a cine acquired from an imaging system. In some examples, the image frames can be from a looped video sequence displayed on a display connected to the imaging system and/or the host device. The image frames include one or more frames acting as a placeholder between other cine acquisitions in a displayed video stream.

The host device tags the initial image frame following a placeholder frame with a timestamp for the initial digital word in the temporal data, according to block 550. The host device can be configured to process the received sequence of image frames to identify the initial frame occurring after a placeholder frame. Placeholder frames can be predetermined to have certain features, such as a full black image, and the host device can be configured to identify that an image frame is a placeholder based on the image frame having those predetermined features. As part of tagging the initial image frame, the host device can determine that the time the host device received the initial image frame corresponds to the time of the initial radiation pulse, plus the video latency value.

The host device identifies the next image frame based on a predetermined interval and the video latency value, according to block 570. Beginning with the second image frame following the initial image frame in the received sequence, the host device can identify the image frame that was received after the initial image frame at a time equal to a predetermined interval plus the video latency value. For example, if the received sequence of image frames is generated at 30 frames per second, then the predetermined interval between images will be approximately 33.33 milliseconds. As another example, image frames generated at 15 frames per second have a predetermined interval of 66.6 milliseconds. The host device can receive data, along with the sequence of image frames, indicating the framerate at which the imaging system generated the images. Because there is video latency between a radiation pulse and the host device receiving the image frame generated from the radiation pulse, the host device checks for the image frame received after the predetermined interval and the video latency value has passed following the initial image frame.

The host device tags the identified image frame with a timestamp of the next digital word in the temporal data, according to block 580. For example, after the initial image frame is tagged, the next digital word in the temporal data corresponds to the occurrence of the second radiation pulse whose scattered radiation is detected by the x-ray detection device. The host device tags the identified image frame with the second digital word.

The host device determines whether the end of the current cine has been reached, according to diamond 590. The host device can determine whether a next image frame after an image frame tagged according to block 570 is not received within a predetermined period of time. The period of time can be the predetermined interval, plus a delta value. The delta value can be predetermined, for example two seconds.

If a host device does not receive an image frame within the predetermined period of time, then the stop time of the current cine is identified as the timestamp for the last tagged image frame in the sequence. The start time for the cine is the time of the first x-ray radiation pulse, i.e., the timestamp for the initial image frame.

If the host device determines that the cine has not ended ("NO"), then the host device can repeat identifying and tagging the next frame, according to blocks 570 and 580. If the host device determines that the cine has ended ("YES"), then the host device ends the process 500.

While the catheterization laboratory or imaging environment may have a user-operated input for starting radiation, e.g., the press of a pedal by the operator's feet, there is a delay between the operator providing the input and the radiation beginning to pulse. Even when a constant latency is predetermined to attempt to account for this delay, determining the occurrence of the initial pulse of radiation for a cine acquisition based on operator input is less accurate than measuring the pulse as it is emitted, as provided for by the x-ray detection device.

Accurate detection of pulses of radiation and accurate generation of temporal data for tagging image frames can be used in a variety of different ways to, for example, improve co-registration processes or to make OCT pullback monitoring more accurate. The host device avoids missing frames or duplicating frames, at least because frames are identified according to the predetermined interval and video latency value, and accurately tagged using the temporal data.

Accurate temporal data tagged to image frames can improve co-registration processes implemented by the host device and relying on accurate temporal data to co-register the angiographic image frames with other types of image frames, such as image frames taken by an imaging probe of a catheter as part of an OCT pullback. For example, the host device can be configured to co-register images of different modalities, e.g., angiographic images and OCT images.

Because only image frames for a current cine acquisition are tagged using temporal data of radiation pulses of a current cine acquisition are determined, the host device can perform co-registration on the image frames without incorrectly processing image frames not part of the current cine.

Accurate determination of the start and stop time of a sequence of radiation pulses as described herein can improve automatic workflow and timing between a cine acquisition and/or other imaging procedures performed in addition to the cine acquisition, such as an OCT pullback.

For example, the temporal data processing engine of a host device can receive data indicating the start and stop time of a sequence of radiation pulses in real-time and provide prompts through the display of the host device for indicating to a user-operator that a cine acquisition is ongoing. In addition, the temporal data processing engine can provide a prompt to the user-operator in real-time to indicate when to begin an OCT pullback, or when to start dye contrast injection as part of an angiographic imaging procedure.

For example, upon receiving the temporal data from the x-ray detection device, the host device can send a prompt to the operator of an imaging system to begin dye contrast injection a predetermined time after the start of the cine acquisition (i.e., according to the timestamp for the initial image frame), The predetermined time after the start of the cine acquisition can be, for example, two seconds. Another predetermined time can be set to start the OCT pullback following the contrast injection. For timing an OCT pullback, the temporal data processing engine can provide, as the cine acquisition is ongoing, whether the OCT pullback timing is invalid or valid. Providing an indication of OCT pullback validity in real-time, instead of after the imaging procedure is over, allows for a faster readjustment of imaging as necessary to provide for a valid OCT pullback. In addition, the temporal data processing engine can automatically prompt the user-operator through the display of the host device to begin an OCT pullback, instead of relying on a manual timing provided through input by the user-operator, which is prone to human error.

Figure 6:
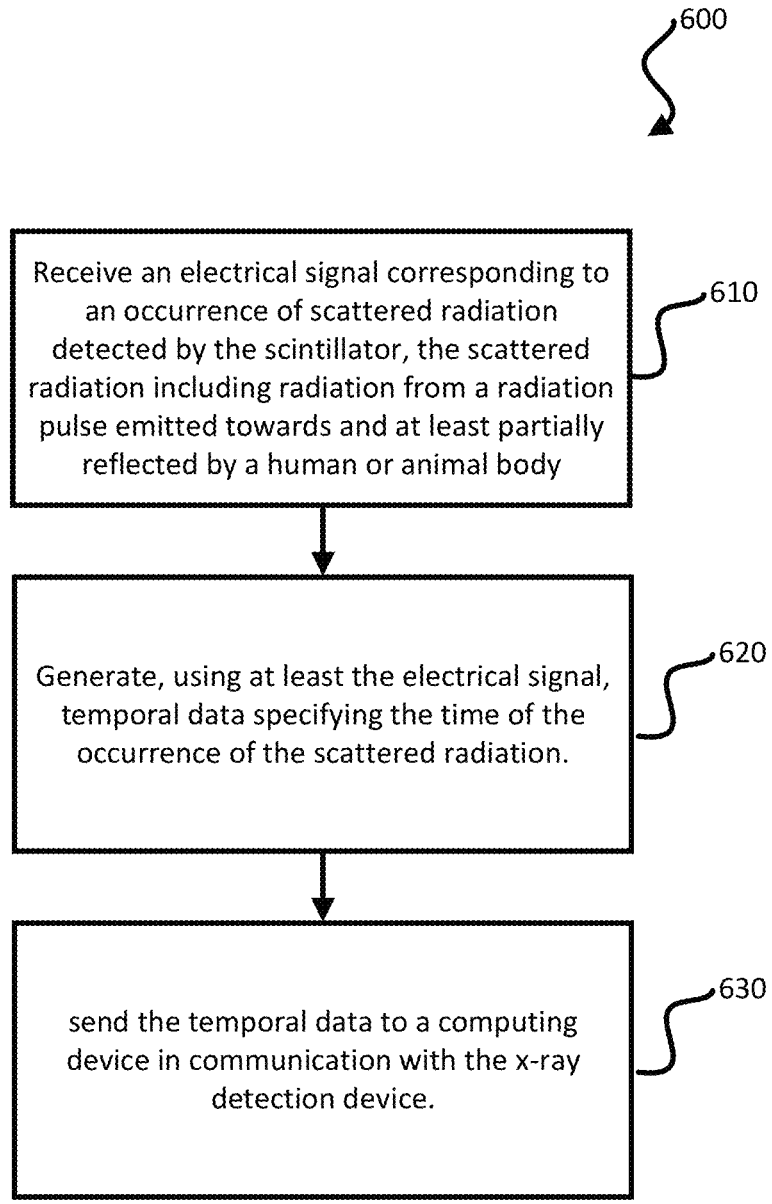
FIG. 6 is a flowchart of an example process for generating temporal data by an x-ray detection device, according to aspects of the disclosure.

FIG. 6 is a flowchart of an example process 600 for generating temporal data by an x-ray detection device, according to aspects of the disclosure.

The x-ray detection device receives an electrical signal corresponding to an occurrence of scattered radiation detected by a scintillator of the x-ray detection device, according to block 610. The x-ray detection device can include a scintillator, a photodiode, and other components for generating the electrical signal, as described herein with reference to FIG. 3A.

The x-ray detection device generates, using at least the electrical signal, temporal data specifying the time of the occurrence of the scattered radiation, according to block 620. The temporal data can include one or more digital words tagged with a respective timestamp. The digital words can represent detected occurrences of scattered radiation, and the timestamps can represent the time at which each occurrence of scattered radiation was detected. As described herein with reference to FIG. 3A, the communication subsystem 330 can include a clock 332 for generating the temporal data at the time of the clock 332 when a digital word corresponding to an electrical signal is received.

The x-ray detection device sends the temporal data to a computing device in communication with the x-ray detection device, according to block 630. For example, the computing device can be a host device, as described herein with reference to FIG. 3B.

Figure 7:
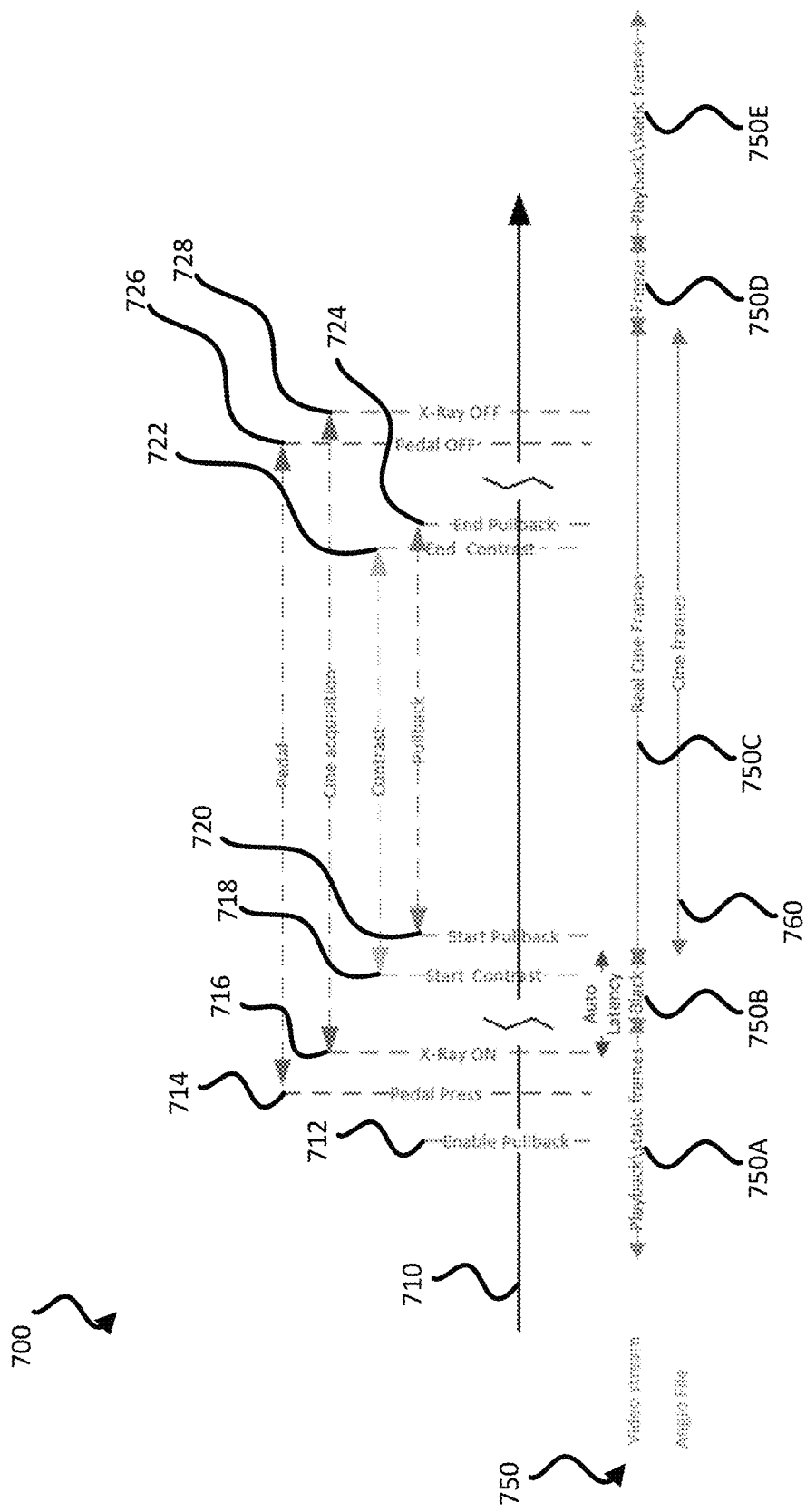
FIG. 7 is a timing diagram illustrating a cine acquisition, according to aspects of the disclosure.

FIG. 7 is a timing diagram 700 illustrating a cine acquisition, according to aspects of the disclosure. Line 710 represents the passage of time, from left-to-right. At line 712, OCT pullback is enabled if OCT imaging is being used concurrently with the cine acquisition. At line 714, a pedal press or other user input is performed by a user-operator of the catheterization laboratory, to begin a sequence of radiation pulses for a cine acquisition. Sometime after the pedal press, at line 714, the beam source begins pulsing radiation. The x-ray detection device can detect the initial pulse of radiation from scattered radiation at line 716, and the host device can calculate the video latency value, as described herein with reference to FIG. 5.

After the first radiation pulse, the host device can send a prompt to start the contrast dye injection, at line 718. As described herein with reference to FIG. 5, by accurately tagging image frames using the temporal data, the host device can facilitate a workflow for adding contrast to the imaged cardiovascular system of the target, which can be co-registered with images taken during an OCT pullback.

At line 720, an OCT pullback starts. As described herein with reference to FIG. 6, based on the accurate detection of when radiation pulses for a cine acquisition begins, the host device can determine whether the pullback is valid or invalid. At line 722, the contrast injection ends. At line 724, the pullback ends. At line 726, a pedal press or other user input is performed by a user-operator of the catheterization laboratory, to end the sequence of radiation pulses for the cine acquisition. At line 728, the beam source is turned off, and the sequence of radiation pulses ends.

Video stream 750 includes image frames received by the host device before, during, and after the cine acquisition between lines 716 and 728. The video stream 750 includes segments 750A-E. The video stream 750 can be generated by an imaging system and received by the host device. Segment 750A can include static frames and/or image frames as part of a playback of a previous cine acquisition, e.g., a cine acquisition occurring before line 712. The host device can playback image frames in a loop on a connected display until a new cine acquisition begins. The segment 750A can end when the beam source for emitting radiation pulses is turned on. Segment 750B can include one or more black frames to separate playback/static frames from image frames in the segment 750A.

Segment 750C includes image frames from a current cine acquisition, e.g., image frames received between the lines 716 and 728 while the beam source of radiation pulses was emitting radiation. The image frames in the segment 750C are tagged using the temporal data received from an x-ray detection device detecting scattered radiation in the time between the lines 716 and 728. The host device can identify the first non-placeholder frame following the placeholder frames in the segment 750B as the initial image frame of the current cine acquisition.

Segment 750D includes one or more freeze image frames. The segment 750D can be a transition in the stream 750 between the current cine acquisition and the playback/static image frames of segment 750E. For example, the one or more freeze image frames can be a replay video of the segment 750C, or a static display of the last image frame tagged in the current cine acquisition.

Segment 750E includes playback/static image frames that the host device can loop on a display until a new cine acquisition begins. The image frames in the segment 750E can include image frames for playback that were originally provided in the tagged image frames in the segment 750C.

Figure 8:
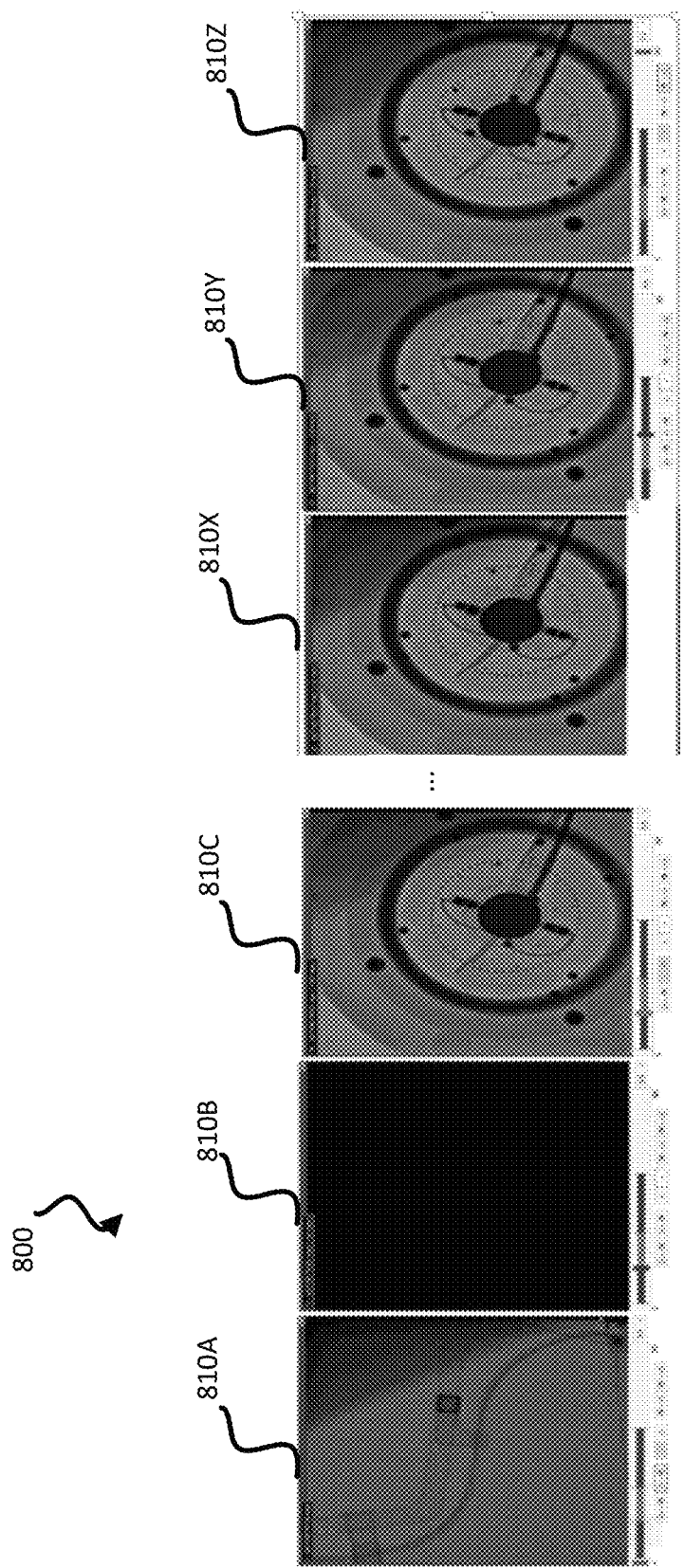
FIG. 8 is a sequence of image frames from an angiography image file tagged with temporal data from an example x-ray detection device.

FIG. 8 is a sequence of image frames 8800 from an angiography image file tagged with temporal data from an example x-ray detection device. The sequence of image frames includes image frames 810A-810Z. The sequence of image frames 800 can be, for example, the video stream 750 as described herein with reference to FIG. 7.

Image frame 810A is an image frame from a cine previously acquired, played back as part of a loop of the video sequence on the display of the host device. Image frame 810B is a black or static frame separating image frames of different cines. Although one black or static frame is shown, the sequence of image frames 800 can include multiple black or static frames in between different cines. Image frames 810C and 810X, and optionally one or more other image frames not shown, make up part of the current cine acquisition. For example, the image frames 810C-810X can be part of the cine frames 760 for the current cine acquisition that are tagged with temporal data generated by an x-ray detection device, as described herein.

Image frames 810Y, 810Z can be part of a playback of the image frames 810C, 810X. As described herein with reference to FIG. 8, image frames of the most recently captured cine can be played-back after the cine acquisition ends. Image frames 810Y, 810Z are not tagged with temporal data, unlike the image frames 810C, 810X, for example because the image frames 810C, 810X were received by the host device during the cine acquisition, while the image frames 810Y, 810Z were received after the cine acquisition ended.

As discussed above, clock 332 of x-ray detection device 100 and clock 375 of host device 301 can be synchronized so that angiographic images can be properly tagged with the temporal data that is collected from x-ray detection device 100. While other forms of synchronization can be used with aspects of the disclosure provided herein, FIGS. 9A-11B illustrate aspects of a synchronization technique that allows for synchronization of clock 332 and clock 375, even when the type of connection between x-ray detection device 100 and host device 301 varies. For example, x-ray detection device 100 and host device 301 may be connected wirelessly, such as through a Bluetooth connection, but may also be connected by other means, including a wired connection, such as via a USB corded connection.

In addition, FIGS. 9A-11B illustrate synchronization techniques that can be used in connection with any devices that contain clocks that are to be synchronized with one another, including other types of devices beyond the x-ray detection and host devices discussed above. For example, the synchronization process described herein may be performed between a personal computer (PC) and a mobile device, such as a watch or mobile phone, so that the clock of the mobile device is synchronized to the PC, or vice versa. Accordingly, the synchronization techniques disclosed herein can be used with any number of applications.

Figure 9A:
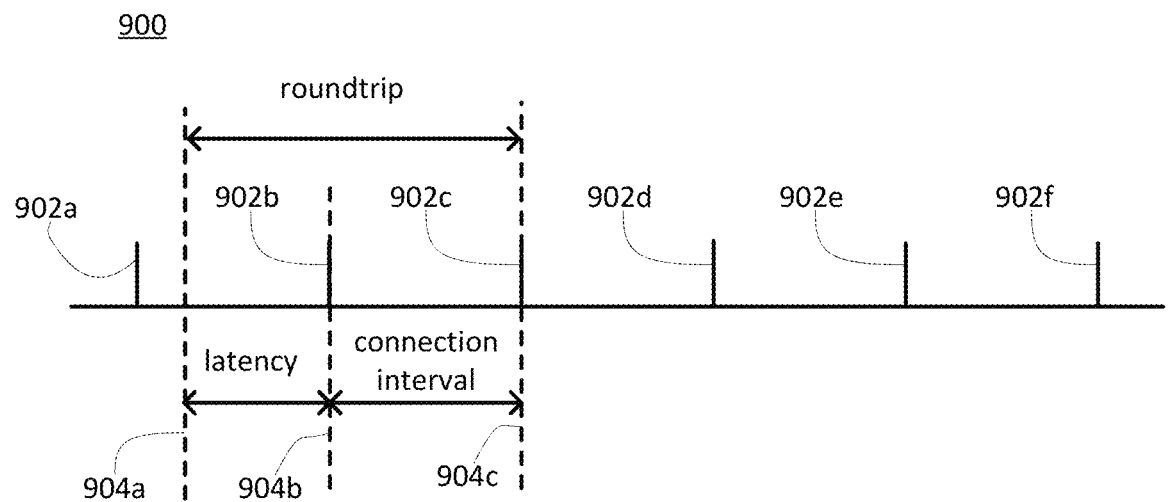
FIGS. 9A-B are charts of device transmissions within connection intervals, according to aspects of the disclosure.

In accordance with aspects of the synchronization techniques described herein, the connection between two devices can be divided into a plurality of connection intervals, wherein each connection interval represents a period of time at which a transmission between the two devices may occur between the two devices. FIG. 9A illustrates a timeline 900 that has been divided into a plurality of connection interval markers 902a-f. Within timeline 900 are event markers 904a, 904b, and 904c that can occur during the transmission of synchronization transmissions between a first and second device. The span from event marker 904a to 904c represents the overall roundtrip time that it takes for synchronization messages to be transmitted between the first and second devices. In particular, the first device can transmit a first synchronization message to a second device, and the second device can transmit a second synchronization message to the first device.

The connection interval of timeline 900 may be based on the type of devices and based on the type of connections between the devices. For example, the connection interval for the devices of timeline 900 may be 200 ms, which means that 200 ms elapses between consecutive interval markers 902. As shown in FIG. 9A, the roundtrip transmission time may include a latency period. This latency period can represent some delay that occurs in relation to the transmission. For example, in timeline 900, the first device resets its clock and writes a synchronization message to a device transmitter (e.g., a device dongle) at event marker 904a, which occurs at a time T1. However, the dongle does not transmit the synchronization message to the second device until a later time corresponding to interval marker 902b. Upon receiving the synchronization message from the first device, the second device may be configured to reset its clock based on the received message to a time T2 and to send a return message to the first device. The second device can be configured so that only a negligible amount of time passes from the time it receives the clock reset message from the first device, and the time at which its clock is reset. The second device may also be configured to account for the amount of time that it requires to reset its clock after receiving a clock reset message. The first device receives the return message at a time T3 in accordance with the event marker 904c.

The latency present in the synchronization transmission of FIG. 9A prevents the clock of the first device from being synchronized with the clock in the second device. In order to synchronize the two clocks, the time T1 for the reset the first device's clock can be adjusted to account for the latency. In particular, the latency value (L) can be determined by subtracting the connection interval (C) from the roundtrip time, which corresponds to T3 minus T1. This can be expressed as follows:

$$L = (T3 - T1) - C$$

Once the latency value L is determined, this value can be added to the time of the first device's clock, so as to synchronize it with the second device's clock. In the example shown in FIG. 9A, the calculation is based on the overall transmission time for the synchronization message being less than two connection intervals. In particular, as shown in FIG. 9A, the latency is less than a connection interval, and the event markers 904b and 904c occur between adjacent interval markers 902b and 902c. Accordingly, for the transmission shown in timeline 900, the roundtrip (T3−T1) is less than two connection intervals (2*C). The transmission of timeline 900, therefore represents an ideal transmission in which the overall transmission time, including the latency, does not cause the roundtrip time to span two connection intervals or more.

Figure 9B:
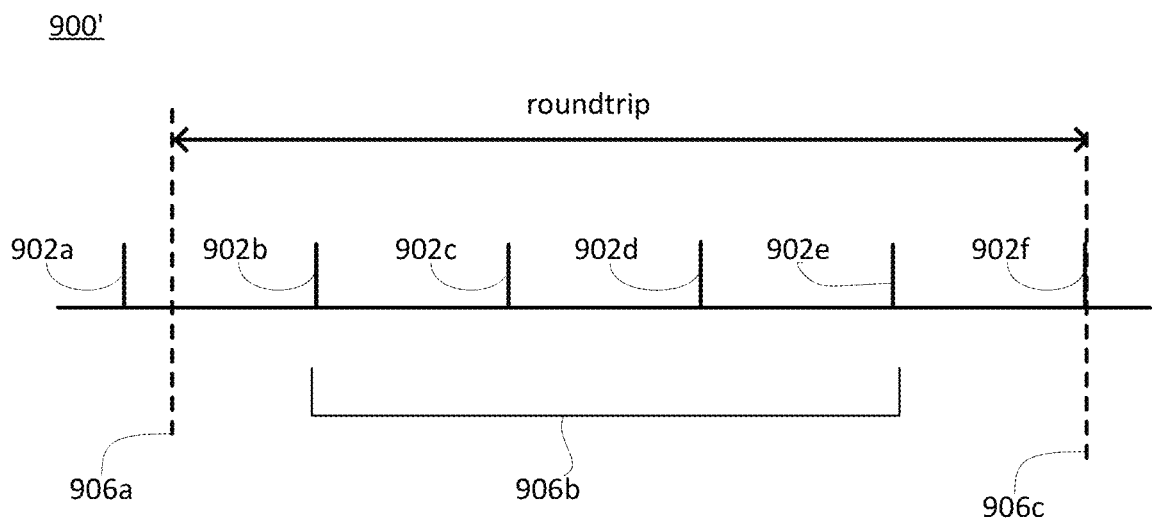

FIG. 9B illustrates a timeline 900', in which the roundtrip time for the synchronization transmission spans more than two connection intervals. In particular, the event marker 906a is between interval markers 902a and 902b, while event marker 906c corresponds with interval marker 902f. Accordingly, the first device's clock is reset at a time T1 that is a some time between the connection intervals corresponding with interval markers 902a and 902b, and the receipt of the synchronization return message occurs at a time T3 that corresponds with interval marker 902f. The second device will have reset its clock to a time T2 based on the receipt of a synchronization message that corresponds to one of the interval markers 902b-902e. The event marker 906b that corresponds with the second device's clock reset at T2 may therefore occur in connection with any one of the interval markers 902b-902e. The latency of the synchronization transmission shown in timeline 900' will therefore be the overall roundtrip time (T3−T1) minus some multiple of the connection interval (C), where the multiple is either 1, 2, 3, or 4. This can be expressed as follows:

$$L = (T3 - T1) - i * C \text{ (where } i = 1, 2, 3, \text{ or } 4)$$

In order to determine that the correct latency value (L) is chosen, the system may check that subsequent transmissions between the first and second devices have event times so that T1<T2+L<T3 is true for even short connection intervals. Thus, by using a short connection interval for subsequent check messages, the correct latency values (L) may be identified. Once this latency value (L) is identified, the reset time ($T_{reset}$) of the first device's clock can be adjusted to an adjusted reset time ($T'_{reset}$), so that $T'_{reset} = T_{reset} + L$. Once this adjustment is made, the times T1'<T2<T3' will be true for all subsequent messages.

Figure 10:
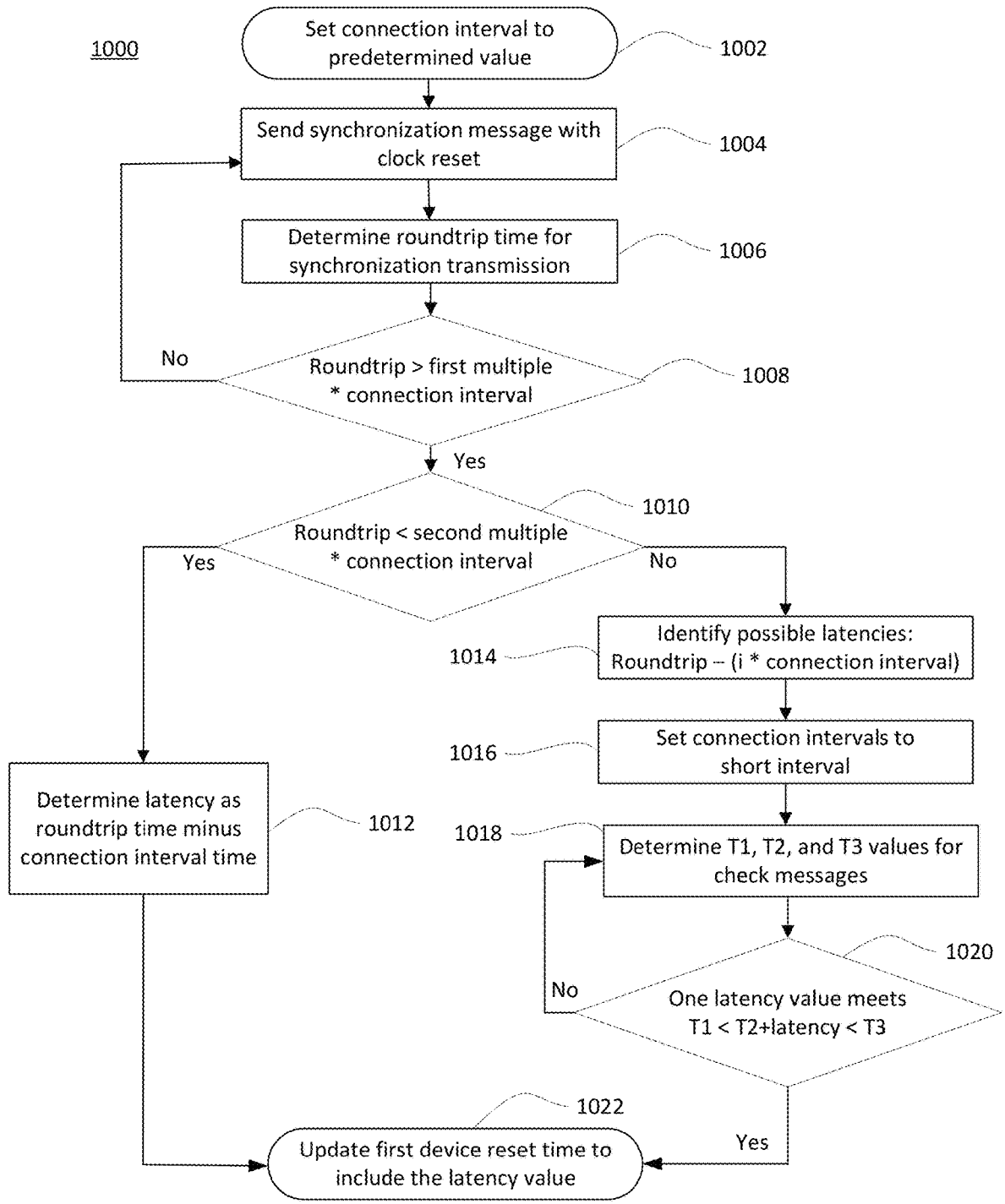
FIG. 10 is a flowchart of an example process for synchronizing device clocks, according to aspects of the disclosure.

FIG. 10 is a flowchart of an example process 1000 for synchronizing the clock of a first device with the clock of a second device in accordance with aspects of the disclosure. At step 1002, a connection interval for the synchronization transmission may be set to a predetermined value, such as for example, 200 ms. A synchronization message for clock reset may be sent at step 1004. As described above, this synchronization message may include a clock reset for the first device corresponding to a time T1, a clock reset for the second device corresponding at a time T2, and a receipt of a return message by the first device corresponding with a time T3. At step 1006, a determination is made of the roundtrip time for the synchronization transmission, where the roundtrip time corresponds to the difference between T1 and T3, so that it can be expressed T3−T1. At step 1008, it can be determined whether the roundtrip time (T3−T1) is greater than a first multiple of the connection interval value. This first multiple can be set to the value of 1, but it need not be a whole number, and may be set to a value such as 1.5. Having a first multiple be around 1.0 or 1.5 allows for a delay when increasing interval values. For example, at step 1002, the connection interval value may be increased from 50 ms to 200 ms. One or more transmissions using the previous 50 ms connection interval may be transmitted before a 200 ms transmission occur. The transmissions using the shorter connection interval can be identified at step 1008, and additional transmissions can be sent at step 1004 until it is determined that the roundtrip time is greater than the selected first multiple, such as 1.0 or 1.5. For example, at step 1008, a determination may be made whether the roundtrip time (T3−T1) is greater than 300 ms, which 1.5 times the connection interval of 200 ms, If it is determined at step 1008 that the synchronization transmission did not have a roundtrip time that was greater than the first multiple of (e.g., 1.5 times) the connection interval, the process can return to step 1004 for another synchronization transmission to be performed. If the roundtrip is greater than the first multiple of the connection interval, a determination may be made at step 1010 whether the roundtrip is less than a second multiple of the connection interval. As discussed above, this second multiple may be set to the value of 2, so that it is determined whether the roundtrip for the synchronization transmission is less than twice the connection interval. If so, the latency associated with the synchronization transmission can be determined to be the roundtrip time of the synchronization transmission minus the predetermined value of the connection interval (step 1012). The latency value determined at step 1012 can be used at step 1022 to update the reset time of the first device's clock. In adjusting the first device's clock by the latency value, the first device's clock can be synchronized to the second device's clock, which was reset at step 1004 to correspond to a time T2 that was affected by the latency of the transmission.

Returning to step 1010, if the roundtrip for the synchronization transmission is not determined to be less than twice the connection interval, the potential latency values are identified at step 1014. As discussed above, the potential latency values (L) are based on the roundtrip (T3−T1) minus some multiple (i) of the connection interval (C), so that L=(T3−T1)−(i*C). At step 1016, a short connection interval may be set for a check message to be transmitted. This short connection interval may be selected so that it is substantially shorter than the predetermined value of the connection interval used at step 1002. For example, the short connection interval may be set to the smallest available value for which a simple check message may be sent, or at least to a value that is small enough so that the values of T1, T2, and T3 of the check message span a time period that allows for the original latency value to be identified. At step 1018, the T1, T2, and T3 values for the simple check messages are determined, and at step 1020 a determination is made as to whether one latency value will meet the criteria for T1<T2+latency<T3 in connection with the simple check message. If not, a determination of T1, T2, and T3 can be made for a new check message at step 1018. If it is determined that only one latency value meets the criteria that T1<T2+latency<T3, then that latency value can be used to update the first device's clock by adjusting the first device's clock by the latency value. In this manner the clocks of the first and second devices may be synchronized.

As described above, the first device and second device may be any devices for which it is desired to have synchronized clocks. In accordance with aspects of the disclosure, the first device may be the host device 301 and the second device may be the x-ray detection device 100.

Once, the clocks of two devices have been synchronized, the two clocks may slowly drift from one another. For example, this drift may be around 0.5 to 0.8 ms per minute. In accordance with aspects of the disclosure, the drift between the two clocks may be corrected, so as to allow for clock synchronization to be maintained over a long period of time. For example, the clock synchronization techniques discussed above can be performed when the two devices are first connected to one another, and then a drift correction can occur thereafter, so as to maintain the clock synchronization.

Figure 11A:
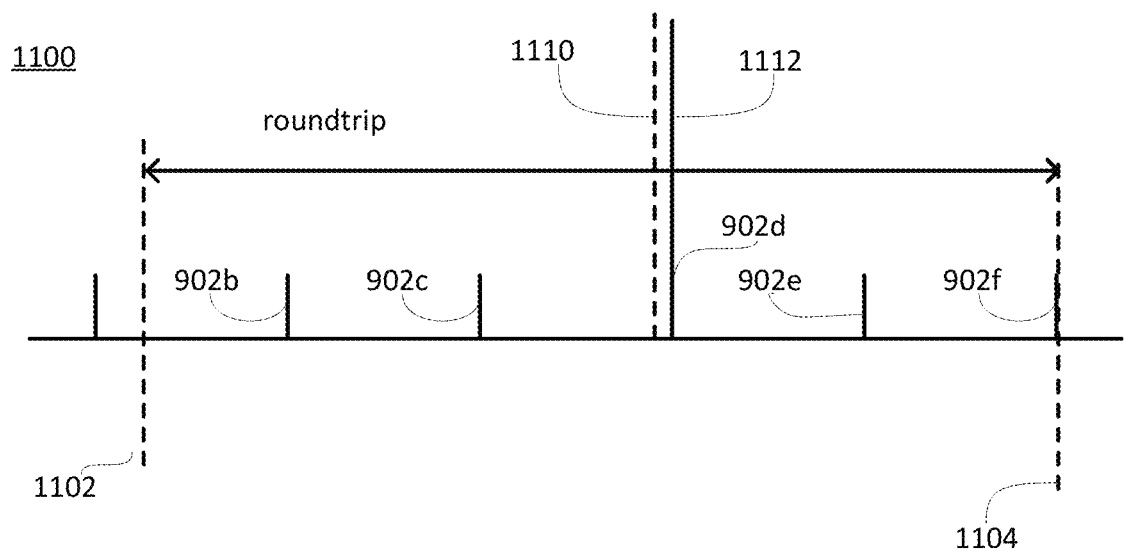
FIGS. 11A-B are charts of device transmissions showing clock drift, according to aspects of the disclosure.

In FIG. 11A, a timeline 1100 of a roundtrip transmission between the first and second device is shown. The roundtrip time corresponds to the time between T1 (event marker 1102), when the first device writes a message to be sent to the second device, and the time T3 (event marker 1104), when the first device receives a return message from the second device. As discussed above, a time T2 corresponds to the time at which the transmission to the second device occurs, and this time T2 will correspond to one of the connection intervals 902b-e that are between event marker 1102 and 1104. However, line 1110 shows the time T2 at which the at which the transmission was actually received by the second device, according to the second device's clock. This line 1110 is slightly off from connection interval marker 902d, due to the drift that has occurred in the second device's clock. Accordingly, the drift of the second device's clock can be determined by determining the difference between the actual received T2 time at line 1110 and the expected received T2 time at line 1112, which is located at the interval marker 902d that is closest to line 1110. The difference in time between line 1110 and 1112 can then be used to correct the drift in the second device's clock. This drift correction technique will remain effective whenever it is performed often enough that the overall drift between corrections is less than half a connection interval. Thus, regularly transmitted messages can be used to maintain synchronization of the clocks for the first and second devices in accordance with the disclosure.

Figure 11B:
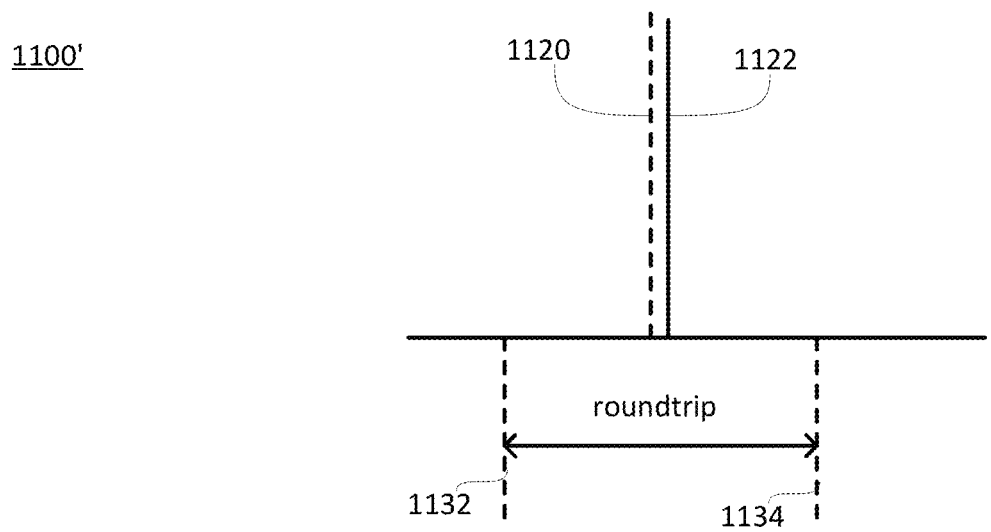

FIG. 11A illustrates a form of drift correction that may be used with transmissions that occurs over a plurality of connection intervals, such as for example, a Bluetooth transmission. FIG. 11B illustrates a drift correction that can be used for other forms of transmission, including a USB connection, which does not have the same latency or plurality of connection intervals as a Bluetooth transmission. With regard to direct transmissions, such as a USB transmission shown in timeline 1100' of FIG. 11B, the expected time T2 for the second device to receive the transmission from the first device can be identified as the halfway point for the roundtrip transmission. Line 1122 represents this expected time T2, which is halfway between line 1132 (corresponding to T1) and line 1134 (corresponding to T3). Line 1120 represents the actual time T2 that is identified by the second device's clock. This drift can be corrected by adjusting the second device clock by an amount that corresponds to the difference between the actual registered time (line 1120) and the expected time (line 1122). In this way, the clocks of the first and second devices may remain synchronized.

Aspects of this disclosure can be implemented in digital circuits, computer-readable storage media, as one or more computer programs, or a combination of one or more of the foregoing. The computer-readable storage media can be non-transitory, e.g., as one or more instructions executable by one or more processors and stored on a tangible storage device.

In this specification the phrase "configured to" is used in different contexts related to computer systems, hardware, or part of a computer program, engine, or module. When a system is said to be configured to perform one or more operations, this means that the system has appropriate software, firmware, and/or hardware installed on the system that, when in operation, causes the system to perform the one or more operations. When some hardware is said to be configured to perform one or more operations, this means that the hardware includes one or more circuits that, when in operation, receive input and generate output according to the input and corresponding to the one or more operations. When a computer program, engine, or module is said to be configured to perform one or more operations, this means that the computer program includes one or more program instructions, that when executed by one or more computers, causes the one or more computers to perform the one or more operations.

While operations shown in the drawings and recited in the claims are shown in a particular order, it is understood that the operations can be performed in different orders than shown, and that some operations can be omitted, performed more than once, and/or be performed in parallel with other operations. Further, the separation of different system components configured for performing different operations should not be understood as requiring the components to be separated. The components, modules, programs, and engines described can be integrated together as a single system or be part of multiple systems. In addition, as described herein, a host device and an x-ray detection device, such as the host device 301 and the x-ray detection device 100, can perform the processes described herein.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The following numbered paragraphs describe features in accordance with various embodiments of the disclosure as further described above:

1. A system comprising:
    one or more processors configured to:
        receive, from an x-ray detection device, temporal data specifying a time of detection of scattered radiation from a radiation pulse emitted towards and at least partially reflected by a human or animal body;
        receive an image frame of a region of the human or animal body; and
        tag the image frame using the temporal data.
2. The system of paragraph 1, wherein the one or more processors are further configured to:
    send the tagged image frame for display on a display device coupled to the one or more processors.
3. The system of any one of paragraphs 1 or 2,
    wherein the one or more processors are further configured to:
        synchronize a host clock coupled to the one or more processors with a device clock of the x-ray detection device; and
        determine a video latency value, the video latency value corresponding to a length of time between receiving an image frame by the one or more processors, and a time of detection of scattered radiation from the radiation pulse.
4. The system of paragraph 3, wherein the one or more processors are further configured to initiate synchronization or determination of the video latency value in response to receiving the temporal data or the image frame.
5. The system of any one of paragraphs 3 or 4, wherein the one or more processors are further configured to:
    after the one or more processors calculate the video latency value, send a prompt for display indicating a start time for contrast injection and a pullback of an imaging probe inside a blood vessel of the human or animal body.
6. The system of any one of paragraphs 3 through 5, wherein the image frame is an initial image frame in a sequence of image frames, the temporal data comprises a sequence of digital words, each digital word indicating an instance of scattered radiation detected by the x-ray detection device, and each digital word tagged with a respective timestamp indicating the time of detection for the scattered radiation,
    wherein the initial image frame is tagged with an initial digital word in the sequence of digital words, and
    wherein the one or more processors are further configured to, for each image frame,
        identify a next image frame in the sequence based on a predetermined interval and a video latency value;
        tag the identified image frame with a timestamp of a next digital word in the sequence of digital words; and
        determine whether the end of the sequence of image frames has been reached.
7. The system of paragraph 6, wherein the predetermined interval is based at least on a frame rate at which the sequence of image frames was generated.
8. The system of any one of paragraphs 6 or 7, wherein the one or more processors are further configured to receive a respective video latency value for each received sequence of image frames.
9. The system of paragraph 8, wherein the video latency value is based at least on a respective operating mode of an imaging system at which the sequence of image frames was generated.
10. The system of any one of paragraphs 6 through 9, wherein to determine whether the end of the sequence of image frames has been reached, the one or more processors are configured to:
    determine that a period of time equal to the predetermined interval plus a predetermined delta value has passed since the last tagged image frame in the sequence of image frames.
11. The system of any one of paragraphs 1 through 10, wherein the one or more processors are configured to communicate wirelessly with the x-ray detection device.
12. The system of any one of paragraphs 1 through 11, wherein the one or more processors are further configured to determine one or both of a start time and a stop time for a sequence of radiation pulses, using at least the temporal data received from the x-ray detection device.
13. The system of any one of paragraphs 1 through 12,
    wherein the image frame is part of a sequence of image frames;
    wherein the one or more processors are configured to receive the sequence of image frames; and
    wherein to tag the image frame of the sequence of image frames with the temporal data, the one or more processors are further configured to determine whether an image frame of the plurality of image frames was received at a time equal to the predetermined interval plus a video latency value after receiving a previous image frame in the sequence of image frames.
14. The system of paragraph 13,
    wherein the one or more processors are configured to tag the image frame of the sequence of image frames while receiving respective temporal data for each of the plurality of radiation pulses.
15. The system of any one of paragraphs 1 through 14,
    wherein the image frame is a first image frame; and
    wherein the one or more processors are further configured to:
        receive a second image frame; and generate data defining a co-registration between the second image frame and the first image frame, using at least the temporal data tagged to the first image frame.

16. The system of paragraph 15, wherein the second image frame was generated according to a modality different from the first image frame.

17. The system of any one of paragraphs 15 or 16, wherein the first image frame is an angiographic image of a portion of a cardiovascular system of the imaged human or animal body, and
wherein the second image frame is an image frame of the portion of the cardiovascular system of the imaged human or animal body taken using optical coherence tomography.

18. A computer-implemented method, comprising:
receiving, by one or more processors and from an x-ray detection device, temporal data specifying a time of detection of scattered radiation from a radiation pulse emitted towards and at least partially reflected by a human or animal body;
receiving, by the one or more processors, an image frame of a region of the human or animal body; and
tagging, by the one or more processors, the image frame using the temporal data.

19. The computer-implemented method of paragraph 18, wherein the method further comprises:
sending, by the one or more processors, the tagged image frame for display on a display device coupled to the one or more processors.

20. The computer-implemented method of any one of paragraphs 18 or 19, wherein the method further comprises:
synchronizing, by the one or more processors, a host clock coupled to the one or more processors with a device clock of the x-ray detection device; and
determining, by the one or more processors, a video latency value, the video latency value corresponding to a length of time between receiving an image frame by the one or more processors, and a time of detection of scattered radiation from the radiation pulse.

21. The computer-implemented method of paragraph 20, wherein the method further comprises:
initiating, by the one or more processors, the synchronizing or the determining of the video latency value in response to receiving the temporal data or the image frame.

22. The computer-implemented method of any one of paragraphs 20 or 21, wherein the method further comprises:
after calculating the video latency value, sending, by the one or more processors, a prompt for display indicating a start time for contrast injection and a pullback of an imaging probe inside a blood vessel of the human or animal body.

23. The computer-implemented method of any one of paragraphs 20 through 22,
wherein the image frame is an initial image frame in a sequence of image frames, the temporal data comprises a sequence of digital words, each digital word indicating an instance of scattered radiation detected by the x-ray detection device, and each digital word tagged with a respective timestamp indicating the time of detection for the scattered radiation,
wherein the initial image frame is tagged with an initial digital word in the sequence of digital words, and
wherein the method further comprises, for each image frame,
identifying, by the one or more processors, a next image frame in the sequence based on a predetermined interval and a video latency value;
tagging, by the one or more processors, the identified image frame with a timestamp of a next digital word in the sequence of digital words; and
determining, by the one or more processors, whether the end of the sequence of image frames has been reached.

24. The computer-implemented method of paragraph 23, wherein the predetermined interval is based at least on a frame rate at which the sequence of image frames was generated.

25. The computer-implemented method of any one of paragraphs 23 or 24, wherein the one or more processors are further configured to receive a respective video latency value for each received sequence of image frames.

26. The computer-implemented method of paragraph 25, wherein the video latency value is based at least on a respective operating mode of an imaging system at which the sequence of image frames was generated.

27. The computer-implemented method of any one of paragraphs 23 through 26, determining whether the end of the sequence of image frames has been reached comprises:
determining, by the one or more processors, that a period of time equal to the predetermined interval plus a predetermined delta value has passed since the last tagged image frame in the sequence of image frames.

28. The computer-implemented method of any one of paragraphs 18 through 27, further comprising communicating wirelessly, by the one or more processors, with the x-ray detection device.

29. The computer-implemented method of any one of paragraphs 18 through 28, wherein the method further comprises determining, by the one or more processors, one or both of a start time and a stop time for a sequence of radiation pulses, using at least the temporal data received from the x-ray detection device.

30. The computer-implemented method of any one of paragraphs 18 through 29,
wherein the image frame is part of a sequence of image frames;
wherein the method further comprises receiving, by the one or more processors, the sequence of image frames; and
wherein tagging the image frame of the sequence of image frames with the temporal data, comprises determining, by the one or more processors, whether an image frame of the plurality of image frames was received at a time equal to the predetermined interval plus a video latency value after receiving a previous image frame in the sequence of image frames.

31. The computer-implemented method of paragraph 30, wherein the method further comprises tagging, by the one or more processors, the image frame of the sequence of image frames while receiving respective temporal data for each of the plurality of radiation pulses.

32. The computer-implemented method of any one of paragraphs 18 through 31,
wherein the image frame is a first image frame; and
wherein the method further comprises:

receiving, by the one or more processors, a second image frame; and generating, by the one or more processors, data defining a co-registration between the second image frame and the first image frame, using at least the temporal data tagged to the first image frame.

33. The computer-implemented method of paragraph 32, wherein the second image frame was generated according to a modality different from the first image frame.

34. The computer-implemented method of any one of paragraphs 32 or 33, wherein the first image frame is an angiographic image of a portion of a cardiovascular system of the imaged human or animal body, and wherein the second image frame is an image frame of the portion of the cardiovascular system of the imaged human or animal body taken using optical coherence tomography.

35. One or more non-transitory computer-readable storage media storing instructions that when executed by one or more processors, cause the one or more processors to perform operations comprising:

receiving from an x-ray detection device, temporal data specifying a time of detection of scattered radiation from a radiation pulse emitted towards and at least partially reflected by a human or animal body;

receiving an image frame of a region of the human or animal body; and tagging the image frame using the temporal data.

36. The computer-readable storage media of paragraph 35, wherein the operations further comprise:

sending, by the one or more processors, the tagged image frame for display on a display device coupled to the one or more processors.

37. The computer-readable storage media of any one of paragraphs 35 or 36, wherein the operations further comprise:

synchronizing, by the one or more processors, a host clock coupled to the one or more processors with a device clock of the x-ray detection device; and determining, by the one or more processors, a video latency value, the video latency value corresponding to a length of time between receiving an image frame by the one or more processors, and a time of detection of scattered radiation from the radiation pulse.

38. The computer-readable storage media of paragraph 37, wherein the operations further comprise:

initiating, by the one or more processors, the synchronizing or the determining of the video latency value in response to receiving the temporal data or the image frame.

39. The computer-readable storage media of any one of paragraphs 37 or 38, wherein the operations further comprise:

after calculating the video latency value, sending, by the one or more processors, a prompt for display indicating a start time for contrast injection and a pullback of an imaging probe inside a blood vessel of the human or animal body.

40. The computer-readable storage media of any one of paragraphs 37 through 39, wherein the image frame is an initial image frame in a sequence of image frames, the temporal data comprises a sequence of digital words, each digital word indicating an instance of scattered radiation detected by the x-ray detection device, and each digital word tagged with a respective timestamp indicating the time of detection for the scattered radiation, wherein the initial image frame is tagged with an initial digital word in the sequence of digital words, and wherein the operations further comprise, for each image frame, identifying, by the one or more processors, a next image frame in the sequence based on a predetermined interval and a video latency value;

tagging, by the one or more processors, the identified image frame with a timestamp of a next digital word in the sequence of digital words; and determining, by the one or more processors, whether the end of the sequence of image frames has been reached.

41. The computer-readable storage media of paragraph 40, wherein the predetermined interval is based at least on a frame rate at which the sequence of image frames was generated.

42. The computer-readable storage media of any one of paragraphs 40 or 41, wherein the one or more processors are further configured to receive a respective video latency value for each received sequence of image frames.

43. The computer-readable storage media of paragraph 42, wherein the video latency value is based at least on a respective operating mode of an imaging system at which the sequence of image frames was generated.

44. The computer-readable storage media of any one of paragraphs 40 through 43, determining whether the end of the sequence of image frames has been reached comprises:

determining, by the one or more processors, that a period of time equal to the predetermined interval plus a predetermined delta value has passed since the last tagged image frame in the sequence of image frames.

45. The computer-readable storage media of any one of paragraphs 35 through 44, wherein the operations further comprise communicating wirelessly, by the one or more processors, with the x-ray detection device.

46. The computer-readable storage media of any one of paragraphs 35 through 45, wherein the operations further comprise determining, by the one or more processors, one or both of a start time and a stop time for a sequence of radiation pulses, using at least the temporal data received from the x-ray detection device.

47. The computer-readable storage media of any one of paragraphs 35 through 46, wherein the image frame is part of a sequence of image frames;

wherein the operations further comprise receiving, by the one or more processors, the sequence of image frames; and wherein tagging the image frame of the sequence of image frames with the temporal data, comprises determining, by the one or more processors, whether an image frame of the plurality of image frames was received at a time equal to the predetermined interval plus a video latency value after receiving a previous image frame in the sequence of image frames.

48. The computer-readable storage media of paragraph 47, wherein the operations further comprise tagging, by the one or more processors, the image frame of the sequence of image frames while receiving respective temporal data for each of the plurality of radiation pulses.

49. The computer-readable storage media of any one of paragraphs 35 through 48,
wherein the image frame is a first image frame; and
wherein the operations further comprise:
receiving, by the one or more processors, a second image frame; and
generating, by the one or more processors, data defining a co-registration between the second image frame and the first image frame, using at least the temporal data tagged to the first image frame.

50. The computer-readable storage media of paragraph 49, wherein the second image frame was generated according to a modality different from the first image frame.

51. The computer-readable storage media of any one of paragraphs 49 or 50,
wherein the first image frame is an angiographic image of a portion of a cardiovascular system of the imaged human or animal body, and
wherein the second image frame is an image frame of the portion of the cardiovascular system of the imaged human or animal body taken using optical coherence tomography.

52. An x-ray detection device, the x-ray detection device comprising:
a scintillator;
a photodiode; and
one or more processors configured to:
receive, from the photodiode, an electrical signal corresponding to an occurrence of scattered radiation detected by the scintillator, wherein the scattered radiation comprises radiation from a radiation pulse emitted towards and at least partially reflected by a human or animal body;
generate, using at least the electrical signal, temporal data specifying a time of the occurrence of the scattered radiation detected by the scintillator; and
send the temporal data to a computing device in communication with the x-ray detection device.

53. The device of paragraph 52, wherein the device is positioned to not occlude or partially occlude the radiation pulse as it is emitted towards the human or animal body.

54. The device of any one of paragraphs 52 or 53, wherein the electrical signal is a first electrical signal, and wherein the one or more processors are further configured to:
receive one or more second electrical signals, each second electrical signal corresponding to a respective occurrence of scattered radiation, and
send the temporal data to the computing device in communication with the x-ray detection device while receiving the one or more second electrical signals.

55. The device of any one of paragraphs 52 through 54, wherein the x-ray detection device comprises a housing and a clip attached to the housing, wherein the clip is formed to connect to an examination table of a catheterization laboratory.

56. The device of any one of paragraphs 52 through 55, wherein the x-ray detection device is configured to detect the occurrence of the scattered radiation while positioned to not occlude or partially occlude the radiation pulse as it is emitted towards the human or animal body.

57. The device of any one of paragraphs 52 through 56, wherein the one or more processors are further configured to:
in response to receiving the electrical signal, sending a request to the computing device to synchronize a clock of the x-ray detection device with a clock connected to the computing device.

The inventio claimed is:

1. A system comprising:
one or more processors configured to:
receive, from an x-ray detection device, temporal data specifying a time of detection of scattered radiation from a radiation pulse emitted towards and at least partially reflected by a human or animal body;
receive an image frame of a region of the human or animal body;
tag the image frame using the temporal data;
synchronize a host clock coupled to the one or more processors with a device clock of the x-ray detection device; and
determine a video latency value, the video latency value corresponding to a length of time between receiving an image frame by the one or more processors, and a time of detection of scattered radiation from the radiation pulse.

2. The system of claim 1, wherein the one or more processors are further configured to:
send the tagged image frame for display on a display device coupled to the one or more processors.

3. The system of claim 1, wherein the one or more processors are further configured to initiate synchronization or determination of the video latency value in response to receiving the temporal data or the image frame.

4. The system of claim 1, wherein the one or more processors are further configured to:
after the one or more processors calculate the video latency value, send a prompt for display indicating a start time for contrast injection and a pullback of an imaging probe inside a blood vessel of the human or animal body.

5. The system of claim 1,
wherein the image frame is an initial image frame in a sequence of image frames, the temporal data comprises a sequence of digital words, each digital word indicating an instance of scattered radiation detected by the x-ray detection device, and each digital word tagged with a respective timestamp indicating the time of detection for the scattered radiation,
wherein the initial image frame is tagged with an initial digital word in the sequence of digital words, and
wherein the one or more processors are further configured to, for each image frame,
identify a next image frame in the sequence based on a predetermined interval and a video latency value;
tag the identified image frame with a timestamp of a next digital word in the sequence of digital words; and
determine whether the end of the sequence of image frames has been reached.

6. The system of claim 5, wherein the predetermined interval is based at least on a frame rate at which the sequence of image frames was generated.

7. The system of claim 5, wherein the one or more processors are further configured to receive a respective video latency value for each received sequence of image frames.

8. The system of claim 7, wherein the video latency value is based at least on a respective operating mode of an imaging system at which the sequence of image frames was generated.

9. The system of claim 5, wherein to determine whether the end of the sequence of image frames has been reached, the one or more processors are configured to:
determine that a period of time equal to the predetermined interval plus a predetermined delta value has passed since the last tagged image frame in the sequence of image frames.

10. The system of claim 1, wherein the one or more processors are configured to communicate wirelessly with the x-ray detection device.

11. The system of any claim 1, wherein the one or more processors are further configured to determine one or both of a start time and a stop time for a sequence of radiation pulses, using at least the temporal data received from the x-ray detection device.

12. The system of claim 1,
wherein the image frame is part of a sequence of image frames;
wherein the one or more processors are configured to receive the sequence of image frames; and
wherein to tag the image frame of the sequence of image frames with the temporal data, the one or more processors are further configured to determine whether an image frame of the plurality of image frames was received at a time equal to the predetermined interval plus a video latency value after receiving a previous image frame in the sequence of image frames.

13. The system of claim 12,
wherein the one or more processors are configured to tag the image frame of the sequence of image frames while receiving respective temporal data for each of the plurality of radiation pulses.

14. The system of claim 1,
wherein the image frame is a first image frame; and
wherein the one or more processors are further configured to:
receive a second image frame; and
generate data defining a co-registration between the second image frame and the first image frame, using at least the temporal data tagged to the first image frame.

15. The system of claim 14, wherein the second image frame was generated according to a modality different from the first image frame.

16. The system of claim 14,
wherein the first image frame is an angiographic image of a portion of a cardiovascular system of the imaged human or animal body, and
wherein the second image frame is an image frame of the portion of the cardiovascular system of the imaged human or animal body taken using optical coherence tomography.

17. A computer-implemented method, comprising:
receiving, by one or more processors and from an x-ray detection device, temporal data specifying a time of detection of scattered radiation from a radiation pulse emitted towards and at least partially reflected by a human or animal body;
receiving, by the one or more processors, an image frame of a region of the human or animal body;
tagging, by the one or more processors, the image frame using the temporal data;
synchronizing, by the one or more processors, a host clock coupled to the one or more processors with a device clock of the x-ray detection device; and
determining, by the one or more processors, a video latency value, the video latency value corresponding to a length of time between receiving an image frame by the one or more processors, and a time of detection of scattered radiation from the radiation pulse.

18. The computer-implemented method of claim 17, wherein the method further comprises:
sending, by the one or more processors, the tagged image frame for display on a display device coupled to the one or more processors.

* * * * *